(12) United States Patent
Lee et al.

(10) Patent No.: US 8,871,480 B2
(45) Date of Patent: Oct. 28, 2014

(54) MUTANT MICROORGANISM WITH ENHANCED SUGAR UTILIZATION AND METHODS FOR PREPARING THE SAME

(75) Inventors: Sung Kuk Lee, Ulsan (KR); Vinuselvi Parisutham, Ulsan (KR)

(73) Assignee: Unist Academy-Industry Research Corporation, Ulsan (KR)

( * ) Notice: Subject to any disclaimer, the term of this patent is extended or adjusted under 35 U.S.C. 154(b) by 0 days.

(21) Appl. No.: 13/981,661

(22) PCT Filed: Feb. 13, 2012

(86) PCT No.: PCT/KR2012/001059
§ 371 (c)(1),
(2), (4) Date: Jul. 25, 2013

(87) PCT Pub. No.: WO2012/108740
PCT Pub. Date: Aug. 16, 2012

(65) Prior Publication Data
US 2013/0309744 A1    Nov. 21, 2013

Related U.S. Application Data

(60) Provisional application No. 61/499,683, filed on Jun. 21, 2011.

(30) Foreign Application Priority Data

Feb. 11, 2011  (KR) .................. 10-2011-0012324
Jul. 19, 2011   (KR) .................. 10-2011-0071557
Dec. 20, 2011  (KR) .................. 10-2011-0138591

(51) Int. Cl.
C12P 1/04    (2006.01)
C12N 1/20    (2006.01)
C12N 15/70   (2006.01)

(52) U.S. Cl.
CPC ..................... *C12N 15/70* (2013.01)
USPC ........................ 435/170; 435/252.8

(58) Field of Classification Search
None
See application file for complete search history.

(56) References Cited

PUBLICATIONS

Kachroo et al., "Mutations that Alter the Regulation of the chb Operon of *Escherichia coli* Allow Utilization of Cellobiose," Molecular Microbiology, 2007, vol. 66, No. 6, pp. 1382-1395.
Hall et al., "Nucleotide Sequence, Function, Activation, and Evolution of the Cryptic asc Operon of *Escheria coli* K12," Mol. Biol. Evol., 1992, vol. 9, No. 4, pp. 688-706.
Vinuselvi et al., "Engineered *Escherichia coli* Capable of Co-Utilization of Cellobiose and Xylose," ScienceDirect.com, http://www.sciencedirect.com/science/article/pii/S0141022911002158, Aug. 1, 2012, 5 pages.
Vinuselvi et al., "Engineering *Escherichia coli* for Efficient Cellobiose Utilization," Appl. Microbiol. Biotechnol., 2011, vol. 92, pp. 125-132.
Chinese Patent Office, Office Action dated May 8, 2014, issued in the Chinese Patent Application No. 201280007996.8.
Parker and Hall "Characterization and Nucleotide Sequence of the Cryptic *cel* Operon of *Escherichia coli* K12", Genetics., Mar. 31, 1990, vol. 124, pp. 455-471.

*Primary Examiner* — Suzanne M Noakes
(74) *Attorney, Agent, or Firm* — Sughrue Mion, PLLC

(57) ABSTRACT

The present invention relates to a mutant microorganism with enhanced sugar utilization and methods for preparing the same. The mutant strain is capable of effectively utilizing various sugars including cellobiose and xylose, and can thus be useful in the production of biofuels, physiologically active materials, medicinal materials or industrial chemicals from cellulosic biomass. It also reduces the need for addition of one out of the three enzymes used in the saccharification of lignocellulose. It also eliminates the need for separate reactors to ferment pentose and hexose sugar.

15 Claims, 23 Drawing Sheets

SEQUENCE LISTING

<160> NUMBER OF SEQ ID NOS: 22

<210> SEQ ID NO 1
<211> LENGTH: 142
<212> TYPE: DNA
<213> ORGANISM: Escherichia coli

<400> SEQUENCE: 1
cttaattatc ttcgcgaatt atttgcccga aatgtgaaga gggtcataac cacaggtcaa        60
ggagaaacaa tttataaggt caaagaaata ctattgctca ggtctatacc gtatactcct       120
ttcagccaca aaaaaagtca tg                                                142

<210> SEQ ID NO 2
<211> LENGTH: 79
<212> TYPE: DNA
<213> ORGANISM: Artificial Sequence
<220> FEATURE:
<223> OTHER INFORMATION: Constitutive promoter CP12

<400> SEQUENCE: 2

```
catatacaag tttattcttg acactagtcg gccaaaatga tataatacct gagtactgtt    60
cacacaggaa acagctatg                                                 79

<210> SEQ ID NO 3
<211> LENGTH: 253
<212> TYPE: DNA
<213> ORGANISM: Escherichia coli

<400> SEQUENCE: 3 cccttttacac gcaatcaacg cagtgtactg caccgtttgc cgattgtcct tgcacaatcg   60
gcgggaaaaa tattcaggtg accggtttca caaatataaa aaatgaacaa ttcactctct  120
tgcttattta gtgacaacta ttcatgattt tgtgaaaccg gtttcttaat tccgtttcag  180
catcggcatt tttccgtcac gtcgactgat aacaactaca tctaccctac tgataacagg  240
ataaaatccg atg                                                     253

<210> SEQ ID NO 4
<211> LENGTH: 47
<212> TYPE: DNA
<213> ORGANISM: Artificial Sequence
<220> FEATURE:
<223> OTHER INFORMATION: SOEing CP12 promoter

<400> SEQUENCE: 4
catagctgtt tcctgtgtga acagtactca ggtattatat cattttg                 47

<210> SEQ ID NO 5
<211> LENGTH: 46
<212> TYPE: DNA
<213> ORGANISM: Artificial Sequence
<220> FEATURE:
<223> OTHER INFORMATION: SOEing CP12 promoter

<400> SEQUENCE: 5
tcaggtatta tatcattttg gccgactagt gtcaagaata aacttg                  46

<210> SEQ ID NO 6
<211> LENGTH: 46
<212> TYPE: DNA
<213> ORGANISM: Artificial Sequence
<220> FEATURE:
<223> OTHER INFORMATION: SOEing CP12 promoter

<400> SEQUENCE: 6
tagtgtcaag aataaacttg tatatgattc cggggatccg tcgacc                  46

<210> SEQ ID NO 7
<211> LENGTH: 870
<212> TYPE: DNA
<213> ORGANISM: Escherichia coli

<400> SEQUENCE: 7
atgaatatgc tggaaaaaat ccagtctcag ctggaacatt tgagcaaatc agagcgcaaa   60
gttgccgagg tcattctggc ttcgcccgat aacgcgatcc attcgagtat gctgctatg   120 gcactggaag ccaatgttag cgaaccgacg gtgaatcgtt tctgtcgcag catggacacg  180
cgcggttttc ctgattttaa acttcatctg gcacagagtc tggcgaatgg cactccctat  240
gttaatcgca atgtcaatga agatgacagc gttgaatcat acacaggaa aatatttgag   300 tccgcaatgg caacgcttga tcatgtccgt cattcactgg ataaatctgc catcaaccgc  360
gccgtcgact tgctcactca ggcaaaaaaa atcgccttt tcggattagg ctcttcagcc   420
```

```
gccgttgccc acgatgcgat gaataagttc tttcgtttta atgttccggt ggtgtactcc    480
gatgatatcg tgctgcaacg catgagttgt atgaattgta gcgacggaga cgtggtggtg    540
ctgatttctc acactggaag aacaaaaaat ctggtcgagc tggcgcagct ggcacgcgaa    600
aacgacgcca tggtgattgc cctcacctct gcgggtaccc cgctcgcccg ggaagcaacg    660
ctggcaatta ccctcgacgt accggaagat actgacattt atatgcccat ggtttctcga    720
cttgcacagc tgaccgtgat agatgtgctg gcgacaggat ttactttgcg acgcggtgca    780
aaattcagag ataacttgaa gcgggtcaaa gaagcgctga aggaatcgcg ttttgataag    840
cagttactta atttaagtga cgatcgctaa                                     870
```

<210> SEQ ID NO 8
<211> LENGTH: 289
<212> TYPE: PRT
<213> ORGANISM: Escherichia coli

<400> SEQUENCE: 8

```
Met Asn Met Leu Glu Lys Ile Gln Ser Gln Leu Glu His Leu Ser Lys
 1               5                  10                  15

Ser Glu Arg Lys Val Ala Glu Val Ile Leu Ala Ser Pro Asp Asn Ala
            20                  25                  30

Ile His Ser Ser Ile Ala Ala Met Ala Leu Glu Ala Asn Val Ser Glu
         35                 40                 45

Pro Thr Val Asn Arg Phe Cys Arg Ser Met Asp Thr Arg Gly Phe Pro
     50                 55                 60

Asp Phe Lys Leu His Leu Ala Gln Ser Leu Ala Asn Gly Thr Pro Tyr
 65                 70                 75                  80

Val Asn Arg Asn Val Asn Glu Asp Asp Ser Val Glu Ser Tyr Thr Gly
                85                  90                  95

Lys Ile Phe Glu Ser Ala Met Ala Thr Leu Asp His Val Arg His Ser
            100                 105                 110

Leu Asp Lys Ser Ala Ile Asn Arg Ala Val Asp Leu Leu Thr Gln Ala
         115                 120                 125

Lys Lys Ile Ala Phe Phe Gly Leu Gly Ser Ser Ala Ala Val Ala His
     130                 135                 140

Asp Ala Met Asn Lys Phe Phe Arg Phe Asn Val Pro Val Val Tyr Ser
145                 150                 155                 160

Asp Asp Ile Val Leu Gln Arg Met Ser Cys Met Asn Cys Ser Asp Gly
                165                 170                 175

Asp Val Val Leu Ile Ser His Thr Gly Arg Thr Lys Asn Leu Val
            180                 185                 190

Glu Leu Ala Gln Leu Ala Arg Glu Asn Asp Ala Met Val Ile Ala Leu
         195                 200                 205

Thr Ser Ala Gly Thr Pro Leu Ala Arg Glu Ala Thr Leu Ala Ile Thr
     210                 215                 220

Leu Asp Val Pro Glu Asp Thr Asp Ile Tyr Met Pro Met Val Ser Arg
225                 230                 235                 240

Leu Ala Gln Leu Thr Val Ile Asp Val Leu Ala Thr Gly Phe Thr Leu
                245                 250                 255

Arg Arg Gly Ala Lys Phe Arg Asp Asn Leu Lys Arg Val Lys Glu Ala
            260                 265                 270

Leu Lys Glu Ser Arg Phe Asp Lys Gln Leu Leu Asn Leu Ser Asp Asp
         275                 280                 285
```

Arg

<210> SEQ ID NO 9
<211> LENGTH: 870
<212> TYPE: DNA
<213> ORGANISM: Artificial Sequence
<220> FEATURE:
<223> OTHER INFORMATION: yebK nucleotide sequence of CP12CHBASC30 strain

<400> SEQUENCE: 9

| | | | | | |
|---|---|---|---|---|---|
| atgaatatgc | tggaaaaaat | ccagtctcag | ctggaacatt | tgagcaaatc | agagcgcaaa | 60 |
| gttgccgagg | tcattctggc | ttcgcccgat | aacgcgatcc | attcgagtat | tgctgctatg | 120 |
| gcactggaag | ccaatgttag | cgaaccgacg | gtgaatcgtt | tctgtcgcag | catggacacg | 180 |
| cgcggttttc | ctgattttaa | acttcatctg | gcacagagtc | tggcgaatgg | cactccctat | 240 |
| gttaatcgca | atgtcaatga | agatgacagc | gttgaatcat | acacagggaa | aatatttgag | 300 |
| tccgcaatgg | caacgcttga | tcatgtccgt | cattcactgg | ataaatctgc | catcaaccgc | 360 |
| gccgtcgact | tgctcactca | ggcaaaaaaa | atcgcctttt | tcggattagg | ctcttcagcc | 420 |
| gccgttgccc | acgatgcgat | gaataagttc | tttcgtttta | atgttccggt | ggtgtactcc | 480 |
| gatgatatcg | tgctgcaacg | catgagttgt | atgaattgta | gcgacggaga | cgtggtggtg | 540 |
| ctgatttctc | acactggaag | aacaaaaaat | ctggtcgagc | tggcgcagct | ggcacgcgaa | 600 |
| aacgacgcca | tggtgattgc | cctcacctct | gcgggtaccc | cgctcgcccg | ggaagcaacg | 660 |
| ctggcaatta | ccctcgacgt | accggaagat | actgacattt | atatgcccat | ggtttctcga | 720 |
| cttgcacagc | tgaccgtgat | agatgtgctg | gcgacaggat | ttactttgcg | acgcggtgca | 780 |
| aaattcagag | ataacttgaa | gcgggtcaaa | gaagcgctga | aggaatcgcg | ttttgataag | 840 |
| cagttactta | atttaagtga | cgatcgctaa | | | | 870 |

<210> SEQ ID NO 10
<211> LENGTH: 79
<212> TYPE: PRT
<213> ORGANISM: Artificial Sequence
<220> FEATURE:
<223> OTHER INFORMATION: YebK amino acid sequence of CP12CHBASC30 strain

<400> SEQUENCE: 10

Met Asn Met Leu Glu Lys Ile Gln Ser Gln Leu Glu His Leu Ser Lys
 1               5                  10                  15

Ser Glu Arg Lys Val Ala Glu Val Ile Leu Ala Ser Pro Asp Asn Ala
                20                  25                  30

Ile His Ser Ser Ile Ala Ala Met Ala Leu Glu Ala Asn Val Ser Glu
            35                  40                  45

Pro Thr Val Asn Arg Phe Cys Arg Ser Met Asp Thr Arg Gly Phe Pro
        50                  55                  60

Asp Phe Lys Leu His Leu Ala Gln Ser Leu Ala Asn Gly Thr Pro
65                  70                  75

<210> SEQ ID NO 11
<211> LENGTH: 70
<212> TYPE: DNA
<213> ORGANISM: Artificial Sequence
<220> FEATURE:
<223> OTHER INFORMATION: yebK del forward primer

<400> SEQUENCE: 11
tttctttcag tgcggaaatc gtcattaccc gtgagtctct ttacatcatg tgtaggctgg       60
agctgcttcg 70

<210> SEQ ID NO 12
<211> LENGTH: 70
<212> TYPE: DNA
<213> ORGANISM: Artificial Sequence
<220> FEATURE:
<223> OTHER INFORMATION: yebK del reverse primer

<400> SEQUENCE: 12
gtataagatt aggacagtga cagtcgtttt tagcgatcgt cacttaaatt attccgggga 60
tccgtcgacc 70

<210> SEQ ID NO 13
<211> LENGTH: 25
<212> TYPE: DNA
<213> ORGANISM: Artificial Sequence
<220> FEATURE:
<223> OTHER INFORMATION: Forward primer for sequencing of yebK

<400> SEQUENCE: 13
ttgtcattaa acacggcaca caggc 25

<210> SEQ ID NO 14
<211> LENGTH: 24
<212> TYPE: DNA
<213> ORGANISM: Artificial Sequence
<220> FEATURE:
<223> OTHER INFORMATION: Reverse primer for sequencing of yebK

<400> SEQUENCE: 14
ttctgcgaag ccttctggac atgt 24

<210> SEQ ID NO 15
<211> LENGTH: 648
<212> TYPE: DNA
<213> ORGANISM: Escherichia coli

<400> SEQUENCE: 15
tttacgcttc gccaacgcca gtgcctcacc aggctgctgc cacggacgat taaacgcccc 60
cacaccaaac atatccgccc cgttccagca gaaggtgtgc cagtagcagg cggcaaaacg 120
caagtgctct tccatacgct tacccaacac cagttcgtcg ggattgtagt gacggaatgc 180
taacgggttt gaggatttat tgaactccat aatcagataa ttcacaagtg tgcgctcgct 240
cgcaaaataa aatggaatga tgaaactggg taattcctcg aagagaaaaa tgcaataagt 300
acaattgcgc aacaaaagta agatctcggt cataaatcaa gaaataaacc aaaaatatta 360
aaactgtcct ctaactacag aaggccctac accatgacca acgttgctgc acacgccaaa 420
gaagtcaaaa taggtatggc gattgatgat ctccgtcttg aacgctggca aaaagatcga 480
gatatctttg tgaaaaaggc agaatctctc ggcgcgaaag tatttgtaca gtctgcaaat 540
ggcaatgaag aaacacaaat gtcgcagatt gaaaacatga taaaccgggg tgtcgatgtt 600
cttgtcatta ttccgtataa cggtcaggta ttaagtaacg ttgtaaaa 648

<210> SEQ ID NO 16
<211> LENGTH: 605
<212> TYPE: DNA
<213> ORGANISM: Artificial Sequence
<220> FEATURE:
<223> OTHER INFORMATION: Constitutive promoter CP25XylAB/CP6XylFGH

<400> SEQUENCE: 16

```
tttacgcttc gccaacgcca gtgcctcacc aggctgctgc cacggacgat taaacgcccc      60
cacaccaaac atatccgccc cgttccagca gaaggtgtgc cagtagcagg cggcaaaacg     120
caagtgctct tccatacgct tacccaacac cagttcgtcg ggattgtagt gacggaatgc     180
taacgggttt gaggatttag ctgtttcctg tgtgaacagt actatgtgat tataccagcc     240
ccctcactac atgtcaagaa taaactgcca aatgtaggct ggagctgctt cgaagttcct     300
atactttcta gagaatagga acttcgaact gcaggtcgac ggatcccgga ataccaacg      360 ttgctgcaca cgccaaagaa gtcaaaatag gtatggcgat tgatgatctc cgtcttgaac     420
gctggcaaaa agatcgagat atctttgtga aaaaggcaga atctctcggc gcgaaagtat     480
ttgtacagtc tgcaaatggc aatgaagaaa cacaaatgtc gcagattgaa acatgataa      540 accggggtgt cgatgttctt gtcattattc cgtataacgg tcaggtatta agtaacgttg     600
taaaa                                                                 605
```

<210> SEQ ID NO 17
<211> LENGTH: 144
<212> TYPE: DNA
<213> ORGANISM: Artificial Sequence
<220> FEATURE:
<223> OTHER INFORMATION: Forward primer for substitution of constitutive
     promoter CP25XylAB/CP6XylFGH

<400> SEQUENCE: 17

```
tgagccttca taacgaacgc gatcgagctg gtcaaaatag gcttgcatag ctgtttcctg      60
tgtgaacagt actatgtgat tataccagcc ccctcactac atgtcaagaa taaactgcca    120
aaggtgtagg ctggagctgc ttcc                                           144
```

<210> SEQ ID NO 18
<211> LENGTH: 67
<212> TYPE: DNA
<213> ORGANISM: Artificial Sequence
<220> FEATURE:
<223> OTHER INFORMATION: Reverse primer for substitution of constitutive
     promoter CP25XylAB/CP6XylFGH

<400> SEQUENCE: 18

```
aagcaggagt gaggtgcaaa gggtgagtag aatgttcttt attttcatag ctgtttcctg      60
tgtgaac                                                               67
```

<210> SEQ ID NO 19
<211> LENGTH: 66
<212> TYPE: DNA
<213> ORGANISM: Artificial Sequence
<220> FEATURE:
<223> OTHER INFORMATION: Forward primer for cloning yebK into pZB
     (yebK-pZB-FP)

<400> SEQUENCE: 19

```
gcgctgcaga ataattttgt ttaactttaa gaaggagata tacatatgaa tatgctggaa      60
aaaatc                                                                66
```

<210> SEQ ID NO 20
<211> LENGTH: 30
<212> TYPE: DNA
<213> ORGANISM: Artificial Sequence
<220> FEATURE:
<223> OTHER INFORMATION: Reverse primer for cloning yebK into pZB
     (yebK-pZB-RP)

```
<400> SEQUENCE: 20
cgctagctta ttagcgatcg tcacttaaat                                        30

<210> SEQ ID NO 21
<211> LENGTH: 24
<212> TYPE: DNA
<213> ORGANISM: Artificial Sequence
<220> FEATURE:
<223> OTHER INFORMATION: Forward primers for RT-PCR of ascB

<400> SEQUENCE: 21
cgccaaccag tctgaaggtg cgtt                                              24

<210> SEQ ID NO 22
<211> LENGTH: 24
<212> TYPE: DNA
<213> ORGANISM: Artificial Sequence
<220> FEATURE:
<223> OTHER INFORMATION: Reverse primer for RT-PCR of ascB

<400> SEQUENCE: 22
ccggagaacg ggctatgcaa cata                                              24
```

MUTANT MICROORGANISM WITH ENHANCED SUGAR UTILIZATION AND METHODS FOR PREPARING THE SAME

CROSS REFERENCE TO RELATED APPLICATIONS

This application is a National Stage of International Application No. PCT/KR2012/001059 filed Feb. 13, 2012, claiming priority based on US Provisional Patent Application No. 61/499,683 filed Jun. 21, 2011, and Korean Patent Application Nos. 10-2011-0012324 filed Feb. 11, 2011, 10-2011-0071557 filed Jul. 19, 2011, and 10-2011-0138591 filed Dec. 20, 2011, the contents of all of which are incorporated herein by reference in their entirety.

FIELD OF THE INVENTION

The present invention relates to a mutant microorganism with enhanced sugar utilization and methods for preparing the same, with particular focus to a mutant microorganism obtained by genetic engineering such as promoter replacement in chb operon and/or asc operon or mutation of yebK gene, or evolutionary adaptation.

BACKGROUND OF THE INVENTION

Due to depletion of petrochemical fuels, development of alternative energy sources has become a hot issue in recent years. As an alternative energy source, ethanol can be produced from cellulosic biomass, which is a renewable and most abundant carbon source stored on earth. Researches have been focused on effective decomposition of cellulose, hemi-cellulose and lignin present in lignocellulosic biomass through screening of novel strains with cellulolytic property as well as improvement of enzymatic saccharification and fermentation process.

Major steps involved in the cellulosic fuel production include i) the enzymatic saccharification of plant biomass into simple carbohydrates carried out by the synergistic action of at least three enzymes (e.g., endoglucanase, exoglucanase and β-glucosidase) and ii) microbial fermentation of these carbohydrates into value-added fuels. Recently, many researches are focused on simultaneous saccharification and fermentation (SSF), which combines enzymatic saccharification and microbial fermentation process in a same reactor, significantly enhancing the efficiency of ethanol production by reducing inhibitory action of the saccharifying enzymes and equipment costs. As enzymatic saccharification is one of the most expensive steps in the overall process, researchers have endeavored to enhance the activity of the enzymes used in the saccharification or to develop novel strains capable of producing these enzymes. Advanced genetic engineering has enabled production of strains for simultaneous saccharification and fermentation by the introduction of genes encoding saccharifying enzymes into the fermentation strain or vice versa. The saccharifying enzyme as a heterogenous gene, however, shows considerably low level of expression, and it also has negative effects on cell growth and metabolism when overexpressed. Therefore, modifying the regulation of the endogenous pathway is considered more advantageous than the use of heterogenous genes.

*E. coli* is one of the most effective microorganisms for lignocellulosic fuel production because of its ability to utilize all sugars derived from hydrolysis of biomass. However, the potential of *E. coli* is limited due to carbon catabolite repression (CCR), i.e., inhibition of biosynthesis of enzymes involved in catabolism of carbon sources other than the preferred one (e.g., glucose) in hydrolysate. Thus, sugars such as xylose and arabinose cannot be metabolized until the depletion of glucose. This preference toward glucose utilization impedes fermentation process by reducing the productivity and affects downstream processes due to unused carbon sources. Composition of sugar mixture obtained from lignocellulosic hydrolysate may vary, but glucose and xylose would occupy a significant portion of them. Therefore, there is still need of developing a mutant *E. coli* with enhanced sugar utilization and capable of utilizing sugars simultaneously without preference in order to improve the cost, efficiency and usability in the cellulosic fuel production.

SUMMARY OF THE INVENTION

It is an object of the present invention to provide a novel mutant microorganism with enhanced sugar utilization.

It is another object of the present invention to provide a method for preparing a mutant microorganism with enhanced sugar utilization.

It is still another object of the present invention to provide a method for producing biofuels, physiologically active materials, medicinal materials or industrial chemicals from biomass by employing the above-mentioned mutant microorganism.

In accordance with one aspect of the present invention, there is provides a mutant microorganism prepared by introducing to a wild-type microorganism a mutation selected from:

(a) replacement of the cryptic promoter of chb operon with an active promoter;

(b) replacement of the cryptic promoter of asc operon with an active promoter; and (c) replacement of the cryptic promoters of chb operon and asc operon with active promoters.

In accordance with another aspect of the present invention, there is provided a method for preparing a mutant microorganism, which comprises:

(a) replacing one or more inactive promoters of chb operon and asc operon with one or more promoters.

The mutant microorganism according to the present invention has enhanced capability to utilize various sugars such as cellobiose and xylose, unlike other microorganisms, and can thus be useful in the production of biofuels, physiologically active materials, medicinal materials or industrial chemicals from cellulosic biomass that is mainly composed of glucose and xylose. In addition, the mutant microorganism is advantageous in that there is no need to use β-glucosidase, one of the three hydrolyzing enzymes (endoglucanase, exoglucanase, and β-glucosidase) which catalyzes the last step of the saccharification process. Cellobiose, the substrate for β-glucosidase is an inhibitor against endoglucanase or exoglucanase. In the above-mentioned mutant, cellobiose will be transported into the cells, which would help prevent inhibition of the enzymatic activity of endoglucanase or exoglucanase. Furthermore, the mutant microorganism can utilize various sugars simultaneously, resulting in improved availability of substrate, removal of CCR, shortened fermentation time, and enhanced fermentation productivity. The mutant also reduces the need for addition of one out of the three enzymes used in the saccharification of lignocelluloses, and eliminates the need for separate reactors to ferment pentose and hexose sugar.

Other features and embodiments of the present invention will be apparent from the following description and the appended claims.

BRIEF DESCRIPTION OF DRAWINGS

FIG. 10A indicates a result for CP12CHBASC, FIG. 10B for CP12CHBASC30, FIG. 10C for CP12CHBASCyebK-, and FIG. 10D for CP12CHBASC30yebK-. In each graph, a symbol (♦) represents cellobiose concentration (ln %), (■) for xylose concentration and (▲) for OD, respectively.

DETAILED DESCRIPTION OF THE INVENTION

Hereinafter, the terms used herein are defined.

The term "operon" as used herein refers to the functioning unit of a genomic DNA containing a cluster of genes under the control of a single regulatory signal or promoter. Each structure and function of "chb operon" and "asc operon" herein are well known in the art.

The term "promoter" as used herein refers to a region of DNA that facilitates the transcription of a particular gene. In addition, "cryptic promoter" refers to a promoter which is not able to serve transcriptional functions owing to various reasons, whereas "active promoter" refers to a promoter that can serve transcriptional functions. Examples of "active promoter" include "inducible promoter" and "constitutive promoter." "Inducible promoter" refers to a promoter which can be induced by the presence or absence of certain factors, and "constitutive promoter" refers to an unregulated promoter that allows for continuous transcription of its associated gene, which can be used interchangeably with the term "constitutive promoter" or "promoter for constitutive expression." The cryptic promoters of chb operon and asc operon in the present invention are well known in the art.

The present invention provides a mutant microorganism prepared by introducing to a wild-type microorganism a mutation selected from:

(a) replacement of the cryptic promoter of chb operon with an active promoter;

(b) replacement of the cryptic promoter of asc operon with an active promoter; and (c) replacement of the cryptic promoters of chb operon and asc operon with active promoters.

In one embodiment of the present invention, there is provided a mutant microorganism which is prepared from a wild-type microorganism by replacing the cryptic promoter of chb operon with an active promoter. The wild-type microorganism may be *E. coli* or other microorganisms having a genome which shares 70% or more homology with that of *E. coli*, for example, *Salmonella*, but not limited thereto.

Figure 1:
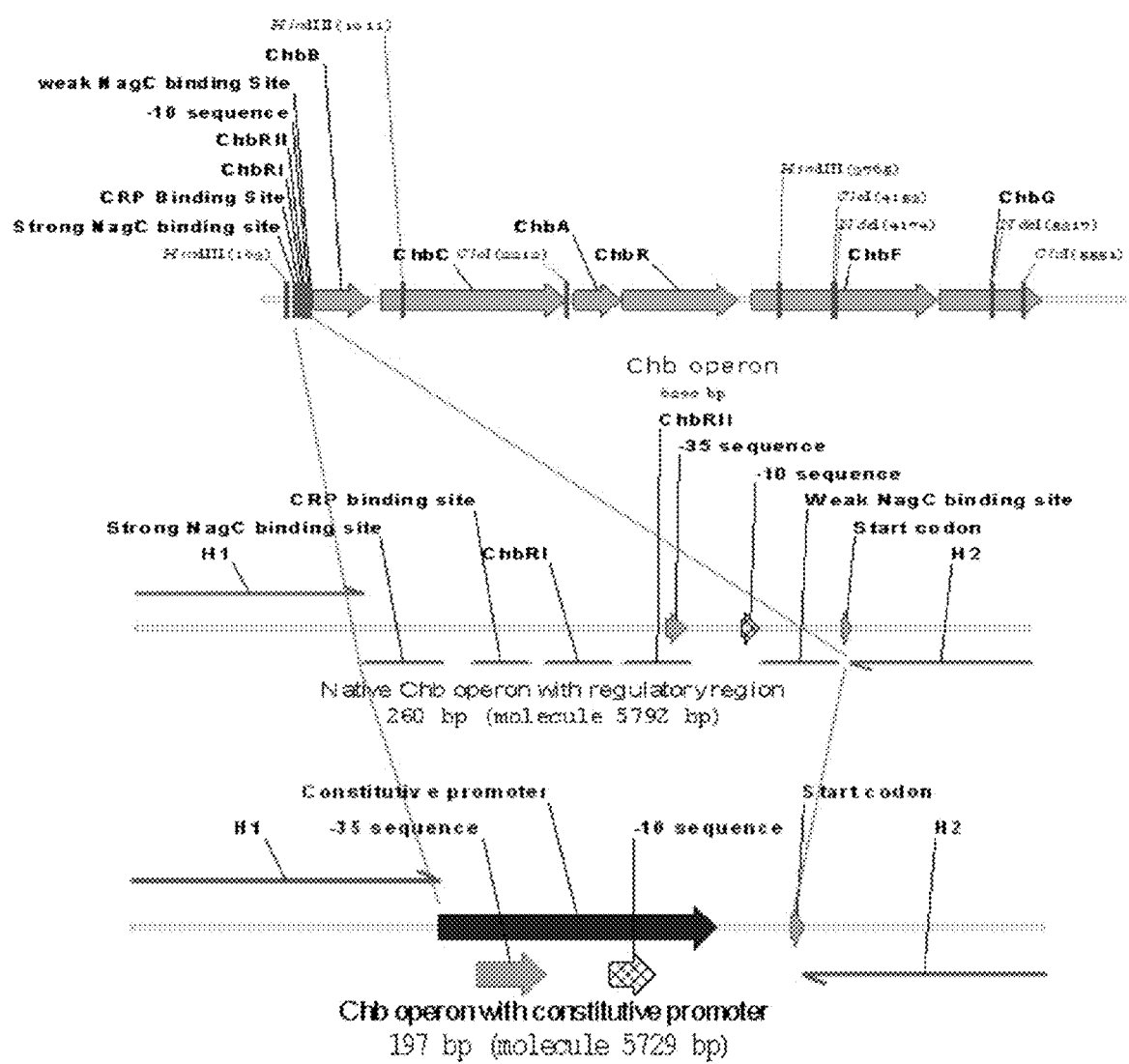
FIG. 1 illustrates the replacement process of the cryptic promoter of chb operon with an active promoter.

The replacement process of the cryptic promoter of chb operon with an active promoter, as described in FIG. 1, can be carried out via Splice Overlap Extension PCR and using λ-Red recombination system, or any other alternative method known to those skilled in the art. The cryptic promoter of chb operon may have the nucleotide sequence of SEQ ID NO: 1; the active promoter used in this present invention may be any promoter known in the art to allow inducible or constitutive transcription of specific genes. In an exemplary embodiment of the present invention, the active promoter may have the nucleotide sequence of SEQ ID NO: 2. The promoter having the nucleotide sequence of SEQ ID NO: 2 is CP12 promoter as disclosed in Jensen P R et al., *Appl. Environ. Microbiol.* 64(1), 82-87, 1998, and is reported to have β-galactosidase activity of 101 miller units in *E. coli*.

Figure 2:
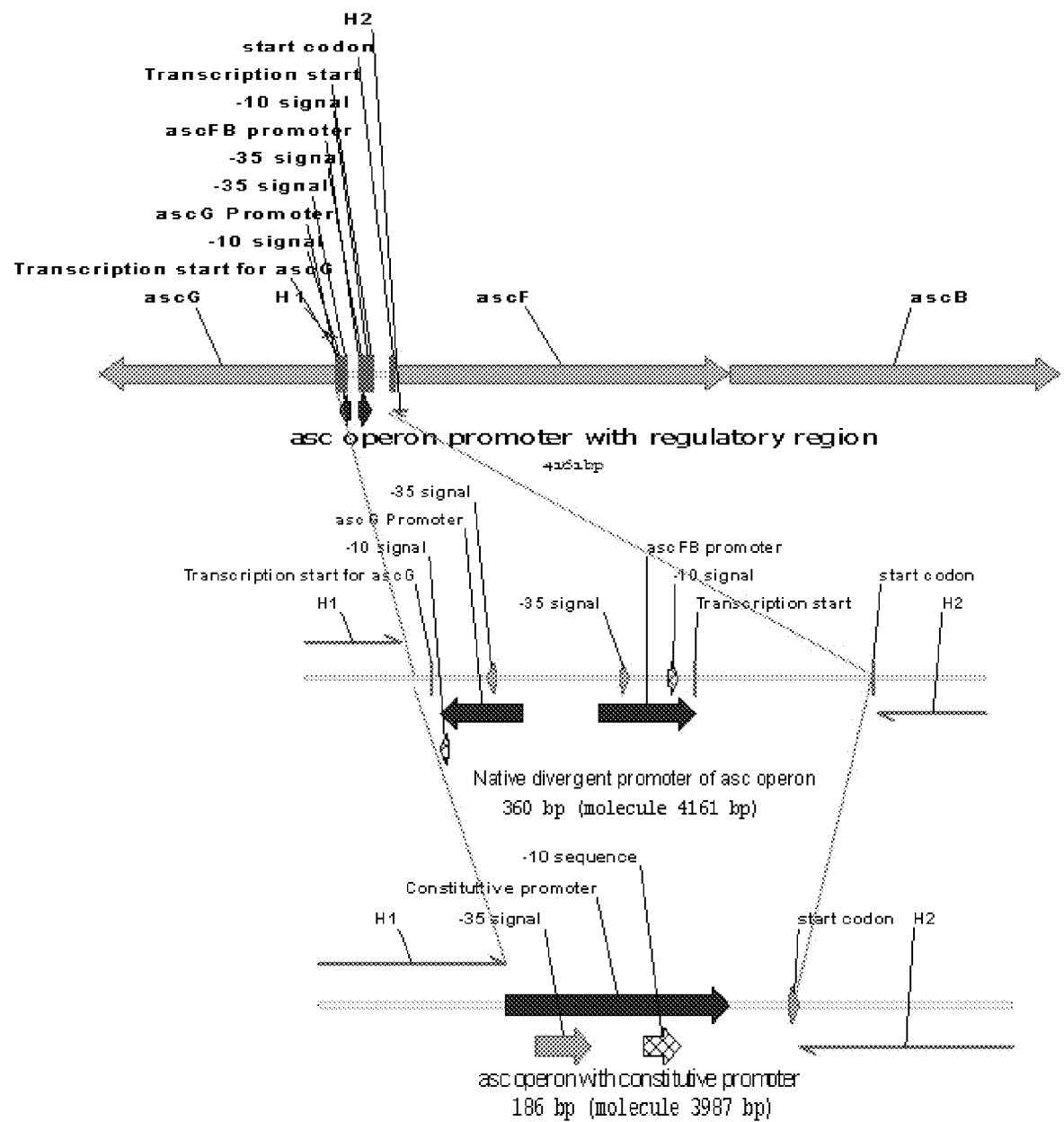
FIG. 2 illustrates the replacement process of the cryptic promoter of asc operon with an active promoter.

In another embodiment of the present invention, there is provided a mutant microorganism which is prepared from a wild-type microorganism by replacing the cryptic promoter of asc operon with an active promoter. The replacement process of the cryptic promoter of asc operon with a well-known active promoter, as described in FIG. 2, can be carried out via Splice Overlap Extension (SOE) PCR and using λ-Red recombination system, or any other alternative method known to those skilled in the art. The cryptic promoter of asc operon may have the nucleotide sequence of SEQ ID NO: 3; the active promoter used in the present invention may be any promoter known in the art to allow inducible or constitutive transcription of specific genes. In an exemplary embodiment of the present invention, the active promoters may have the nucleotide sequence of SEQ ID NO: 2.

In another embodiment of the present invention, there is provided a mutant microorganism which is prepared from a wild-type microorganism by replacing the cryptic promoters of chb operon and asc operon with active promoters.

The active promoters of mutant microorganism allow activation of one or more cryptic genes in chb operon and/or asc operon, conferring an efficient cellobiose utilization phenotype.

The mutant microorganism of the present invention can be further modified by:

(d) mutation of yebK gene, wherein an intact protein is not expressed from the mutated yebK gene.

The yebK gene is also known as hexR and was registered in GenBank under Accession No. NC_000913.2 (EG12860; EcoCyc; b1853; ECK1854). The nucleotide sequence of yebK gene is set forth in SEQ ID NO: 7, and the amino acid sequence of YebK protein is set forth in SEQ ID NO: 8.

The mutant microorganism of the present invention exhibits improved cellobiose utilization and simultaneous utilization of other sugars (such as xylose, mannose, galactose and arabinose) owing to the mutation of yebK gene from which an intact protein is not expressed. The mutation may include any mutation whereby no YebK protein is expressed. In an exemplary embodiment of the present invention, such mutation may be carried out by one or more point mutations. Further, in another exemplary embodiment of the present invention, such mutation may be carried out by one or more deletions. Examples of point mutations include CP12CHBASC30 strain in accordance with the present invention. In the CP12CHBASC30 strain, a 240$^{th}$ nucleotide in the yebK gene represented by SEQ ID NO: 7 is substituted with a A instead of a T (see SEQ ID NO: 9), forming a termination codon and consequently producing only N-terminal region of YebK protein. Thus, yebK gene point mutation improves cellobiose utilization of microorganisms and also allows them to utilize both cellobiose and xylose simultaneously (see FIG. 3). Meanwhile, examples of deletion mutation in the present invention include CP12CHBASCyebK- and CP12CHBASC30yebK- strains. The yebK genes in these strains are completely deleted and thereby the strains can have improved cellobiose utilization and simultaneous utilization of other sugars (e.g., xylose, mannose, galactose and arabinose) (see FIGS. 5 and 8). Therefore, the mutation of yebK gene activates metabolic pathway of cellobiose, pentose phosphate pathway and metabolic pathway of hexose. The term "sugar" as used herein refers to cellobiose, xylose, glucose, mannose, galactose, arabinose, etc.

In another embodiment of the present invention, the mutant microorganism may be subjected to evolutionary adaptation by being cultured in a cellobiose minimal medium for at least 30 days. The term "cellobiose minimal medium" refers to a medium containing cellobiose as the only carbon source. Preferably, it may be an M9 minimal medium supplemented with 2 mM $MgSO_4$, 0.1 mM $CaCl_2$ and 1 g/L to 8 g/L of cellobiose, but not limited thereto. Moreover, the adaptation period shall be minimal adaptation period that may affect utilization of sugars including xylose and cellobiose, which may exceed 30 days. In an exemplary embodiment, the adaptation period may be 10 to 90 days.

Conventional wild-type microorganisms, including wild-type *E. coli* cannot utilize cellobiose, and publicly known mutant microorganisms cannot also utilize cellobiose and xylose simultaneously due to carbon catabolite repression (CCR), causing difficulties in production of various chemicals such as, amino acids, biofuels, biopolymers, bioalcohols, recombinant proteins, and the others. On the contrary, the mutant microorganism of the present invention is capable of utilizing cellobiose (one of major saccharides of lignocelluloses biomass) and other sugars (such as xylose, mannose, galactose and arabinose) simultaneously, which is advantageous in production of aforementioned chemicals, because it can improve fermentation efficiency, production yield and costs.

Meanwhile, the present invention provides a method for preparing a mutant microorganism, which comprises:

(a) replacing one or more cryptic promoters of chb operon and asc operon with one or more active promoters.

The replacement process of promoter is the same as stated above.

In one embodiment of the present invention, the method may further comprise:

(b) mutating yebK gene, wherein an intact protein is not expressed from the mutated yebK gene.

The mutation process of yebK gene is the same as stated above.

In another embodiment of the present invention, the method may further comprise:

(c) culturing the mutant microorganism in a cellobiose minimal medium for at least 30 days.

Furthermore, the present invention provides a method for producing biofuels, physiologically active materials, medicinal materials or industrial chemicals by employing the mutant microorganism according to the present invention. Biomass as stated above may preferably be a cellulosic biomass, more preferably lignocellulosic biomass. Processes of biofuel production from biomass are well known to those skilled in the art, and the present invention includes using the mutant microorganism of the present invention in enzymatic saccharification and fermentation process. In one aspect of the present invention, the mutant microorganism according to the present invention can be used in the saccharification process instead of saccharifying enzyme (β-glucosidase) in the saccharification process. Further, in another aspect of the present invention, the mutant microorganism of the present invention can be used in the fermentation process. Moreover, the mutant microorganism according to the present invention can be used in simultaneous saccharification and co-fermentation (SSF) which carry out both saccharification and fermentation in one reactor especially fermentation of both pentose and hexose sugars in the same reactor.

Furthermore, the mutant microorganism according to the present invention can be used to produce various chemicals such as amino acids, biofuels, biopolymers, bioalcohols and recombinant proteins.

EXAMPLES

Hereinafter, the present invention is described in more detail. The following Examples are given for the purpose of illustration only, and are not intended to limit the scope of the invention.

Example 1

**Preparation of Modified *E. Coli* Whose Cryptic Promoter of chb Operon is Replaced with Active Promoter**

As described below, a mutant *E. coli* was prepared from wild-type *E. coli* by replacing the cryptic promoter of chb operon with a constitutive promoter (CP12), a kind of active promoter, and the mutant *E. coli* was designated "CP12CHB".

The only cryptic promoter (SEQ ID NO: 1) of chb operon on *E. coli* MG1655 chromosome was replaced with a synthetic constitutive promoter, CP12 promoter (SEQ ID NO: 2) by using λ-Red recombination system (Datsenko et al., *Proceedings of the National Academy of Sciences of the United States of America*, 97(12), 6640-6645, 2000). The CP12 promoter is described in Jensen P R et al., *Appl. Environ. Microbiol.* 64(1), 82-87, 1998), and is reported to have β-galactosidase activity of 101 miller unit in *E. coli*.

Specifically, for promoter replacement, two overlapping fragments were amplified via Splice Overlap Extension (SOE) PCR to allow the CP12 promoter to be connected with the kanamycin cassette, as described in Datsenko et al. Fragment 1 has the constitutive CP12 promoter in the downstream region of chb operon by using three SOEing CP12 promoters (SEQ ID NOs: 4 to 6) listed in the TABLE 1 and carrying a homologous sequence that can be connected to Fragment 2 in the front region of the CP12 promoter. Fragment 2 has the kanamycin cassette from pKD13 with an overhang that is homologous to the upstream region of the endogenous promoter in chb operon and it has a homologous sequence that can be connected to Fragment 1. The SOE PCR was conducted under the following conditions: 98° C. for 3 min; 30 cycles of 95° C. for 30 sec, 50~60° C. for 30 sec and 72° C. for 2 min. The process is briefly described in FIG. 1, and SOEing CP promoters and plasmids used in the process are listed in the Table 1.

Cells carrying the λ-Red system under araBAD promoter (pKD46) were induced with 10 mM arabinose, made electrocompetent and transformed with the PCR products. Colonies carrying kanamycin resistance were selected, then PCR-amplified and sequenced to confirm site specific insertions and deletions. The strain constructed via aforementioned process was designated "CP12CHB".

Example 2

**Preparation of Modified *E. Coli* Whose Cryptic Promoter of asc Operon is Replaced with Active Promoter**

As described below, a mutant *E. coli* was prepared from wild-type *E. coli* by replacing the cryptic promoter of asc operon with a constitutive promoter (CP12), a kind of active promoter, and the mutant *E. coli* was designated "CP12ASC".

The only cryptic promoter (SEQ ID NO: 3) in asc operon found on chromosome of *E. coli* MG1655 was replaced with the synthetic constitutive promoter, CP12 promoter (SEQ ID NO: 2), in a similar manner with Example 1.

Specifically, for promoter replacement, two overlapping fragments were amplified via Splice Overlap Extension (SOE) PCR to allow the CP12 promoter to be connected with the kanamycin cassette, as described in Datsenko et al. Fragment 1 has the constitutive CP12 promoter in the downstream region of asc operon by using three SOEing CP12 promoters (SEQ ID NOs: 4 to 6) listed in the TABLE 1 and carrying a homologous sequence that can be connected to Fragment 2 in the front region of the CP12 promoter. The SOE PCR was conducted under the following conditions: 98° C. for 3 min; 30 cycles of 95° C. for 30 sec, 50~60° C. for 30 sec and 72° C. for 2 min. The process is briefly described in FIG. 2, and SOEing CP promoters and plasmids used in the process are listed in the Table 1.

Cells carrying the λ-Red system under araBAD promoter (pKD46) were induced with 10 mM arabinose, made electrocompetent and transformed with the PCR products. Colonies carrying kanamycin resistance were selected, then PCR-amplified and sequenced to confirm site specific insertions and deletions. The strain obtained by transformation with the PCR product was designated "CP12ASC".

TABLE 1

| Promoter and Plasmid | Structure/Sequence | Note |
|---|---|---|
| SOEing CP12 Promoter | 5'-CATAGCTGTTTCCTGTGTGAACAGTACTCAGGTATTATATCATTTTG-3' | SEQ ID NO: 4 |
| | 5'-TCAGGTATTATATCATTTTGGCCGACTAGTGTCAAGAATAAACTTG-3' | SEQ ID NO: 5 |
| | 5'-TAGTGTCAAGAATAAACTTGTATATGATTCCGGGGATCCGTCGACC-3' | SEQ ID NO: 6 |
| pKD46 | λ-Red recombinase expression plasmid; temperature-sensitive replication | Datsenko and Wanner 2000 |
| pKD13 | Template plasmid for gene disruption. The resistance gene is flanked by FRT sites. oriR6K-gamma origin requiring the pir+ *E. coli*. | Datsenko and Wanner 2000 |

Example 3

Preparation of Modified *E. Coli* Whose Cryptic Promoters of chb Operon and asc Operon are Replaced with Active Promoters As described in Example 1 and 2, a mutant *E. coli* was prepared from wild-type *E. coli* by replacing the cryptic promoters of chb operon and asc operon with constitutive promoters, and the mutant *E. coli* was designated "CP12CHBASC".

Comparative Example 1

Preparation of Modified *E. Coli* with Mutated cAMP-CRP*

In order to obtain strains with crp* gene (a mutated form of crp gene), the crp gene of the "CP12CHBASC" strain from Example 3 was deleted according to Datsenko et al., and the crp* gene was generated by SOE-PCR ($127^{th}$ amino acid 'T' in CRP gene of *E. coli* strain W3110 was replaced with 'I'). Then, the crp* gene was inserted to the site where the crp gene were removed via the aforementioned replacement method as in Examples 1 or 2. Strains with crp* were isolated based on the fact that mutant strains with crp* exhibit high growth rate compared to strains with crp gene deleted, and were confirmed by PCR amplification and sequencing of DNA. The confirmed strain was designated "CP12CHBASC/CRP*".

Example 4

Constitutive Expression of Modified *E. Coli* (1)

β-Glucosidase assay was performed on the modified *E. coli* CP12CHB, CP12ASC and CP12CHBASC prepared in Examples 1 to 3 to confirm constitutive expression. In brief, the strains were cultured in LB medium at 37° C. overnight, respectively. Then, 2 ml of the cell was lysed and suspended in 200 μL of 50 mM sodium phosphate buffer (pH 7.0). 100 μL of this crude cell extract was incubated with 400 μL of 10 mM p-nitrophenyl-β-glucopyranoside (PNPG) at 37° C. for 2 hours. 1 ml of 1M $Na_2CO_3$ was added thereto to stop the reaction and the absorbance was measured at 410 nm. One unit of the enzyme was defined as the amount of enzyme that liberated 1 μM of p-nitrophenol per minute. The absorbance was measured using a Biochrom Libra S22 spectrophotometer. The measurement was repeated three times and the results are shown in FIG. 3.

Figure 3:
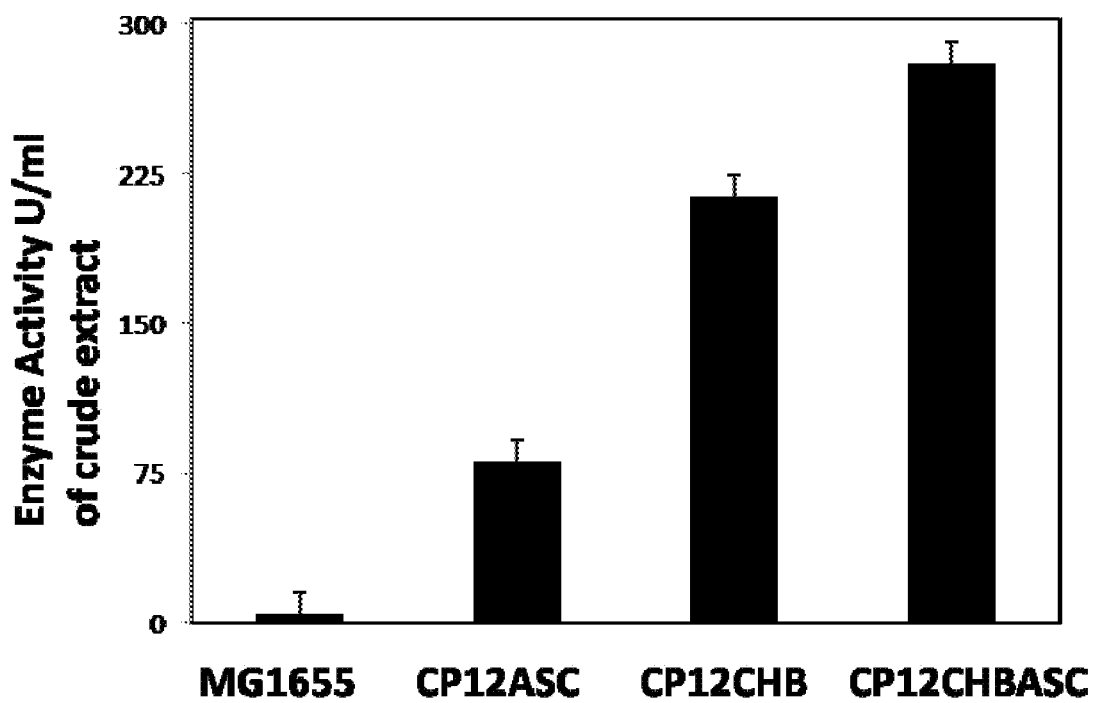
FIG. 3 shows β-glucosidase activities (U/mL) of CP12CHB, CP12ASC and CP12CHBASC, and wild-type MG1655 in LB medium.

As shown in FIG. 3, it was confirmed that the strains with promoter replacement can constitutively express β-glucosidase differently from wild-type MG1655. In particular, the strain whose cryptic promoters of both chb and asc operons are replaced showed the highest constitutive expression.

Example 5

Constitutive Expression of Modified *E. Coli* (2)

β-Glucosidase assay was performed on the modified *E. coli* "CP12CHBASC" prepared in Example 3 to compare constitutive expression in different media. The experiment was the same as in Example 4, and as media, LB medium, M9 medium supplemented with glucose, and M9 medium supplemented with cellobiose were used. The results are shown in FIG. 4.

Figure 4:
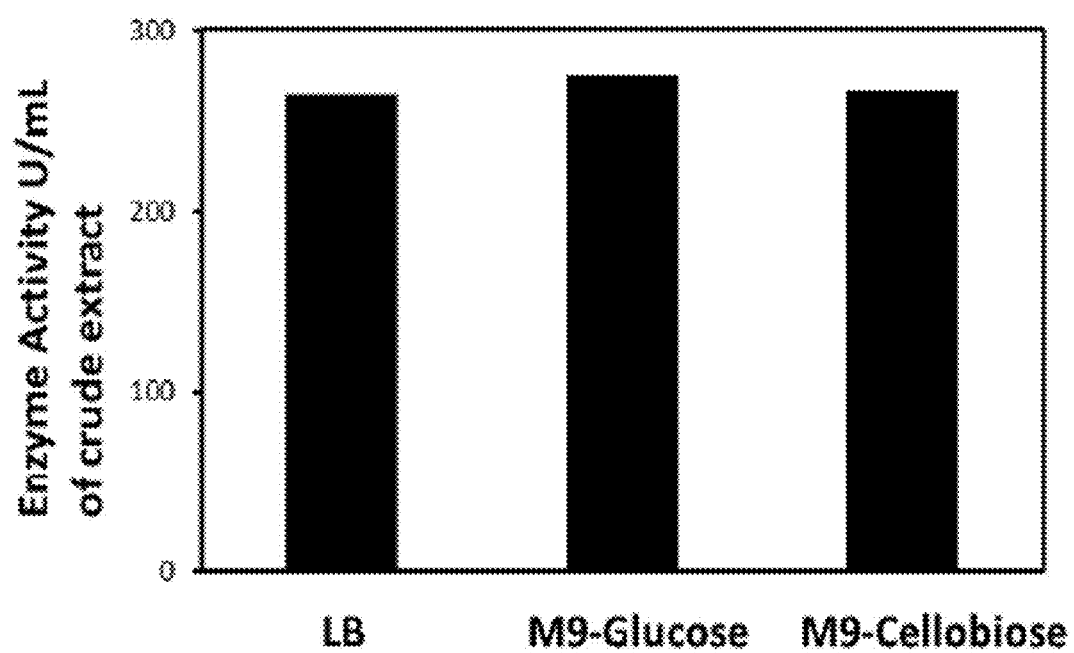
FIG. 4 shows β-glucosidase activities (U/mL) of CP12CHBASC in different culture media (LB, M9-Glucose and M9-Cellobiose).

As shown in FIG. 4, it was confirmed that β-glucosidase is constitutively expressed with the aid of the constitutive promoter, regardless of types of media.

Example 6

Growth Rate of Modified *E. Coli*

The "CP12CHB" and "CP12CHBASC" prepared in Examples 1 and 3, and wild type MG1655 were tested for their growth rates. The "CP12CHB", "CP12CHBASC" and wild-type MG1655 were cultured in a cellobiose minimal medium containing 4 g/L of cellobiose, and another wild-type MG1655 was cultured in a glucose minimal medium containing 4 g/L of glucose, and the growth rates were assayed according to the culture period.

Figure 5:
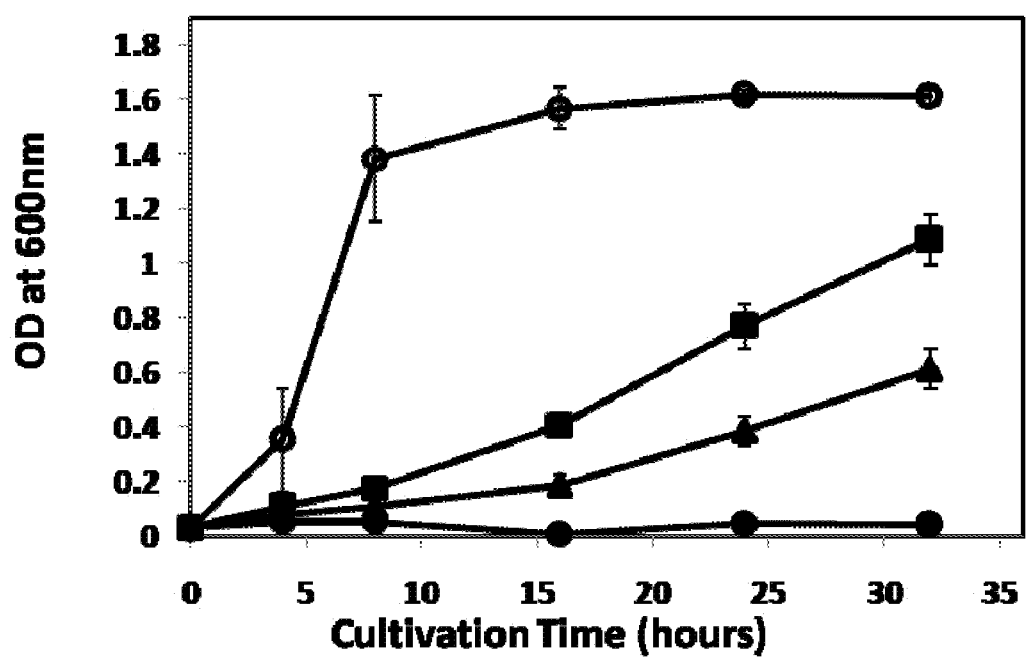
FIG. 5 shows growth rates of CP12CHB (▲), CP12ASC (■), and wild-type MG1655 (●: when cultured in a cellobiose minimal medium; ○: when cultured in a glucose minimal medium).

The results are shown in FIG. 5. As shown in FIG. 5, the wild-type MG1655 could not grow in a cellobiose minimal medium, whereas the strains with promoter replacement showed steady growth according to the culture period. The results indicate that the promoter replacement of chb and/or asc operon can contribute to enhance the utilization of cellobiose.

Example 6

Cellobiose and Xylose Utilization of Modified *E. Coli*

The "CP12CHBASC" obtained in Example 3 and "CP12CHBASC/CRP*" obtained in Comparative Example 1 were assayed for cellobiose and xylose utilization. Each strain was seeded into 50 ml of a M9-minimal medium containing cellobiose (1 g/L) and xylose (1 g/L). The cultured medium was collected at a predetermined time intervals and the residual concentrations of cellobiose and xylose were measured using a Shimadzu HPLC station equipped with HPX-87P (Bio-Rad) column and refractive index detector (Shimadzu). HPLC-grade water was used as mobile phase at the flow rate of 0.6 mL/min. The oven temperature was set to 80° C. A standard curve was determined based on the measurements on different concentration of xylose and cellobiose.

Figure 6:
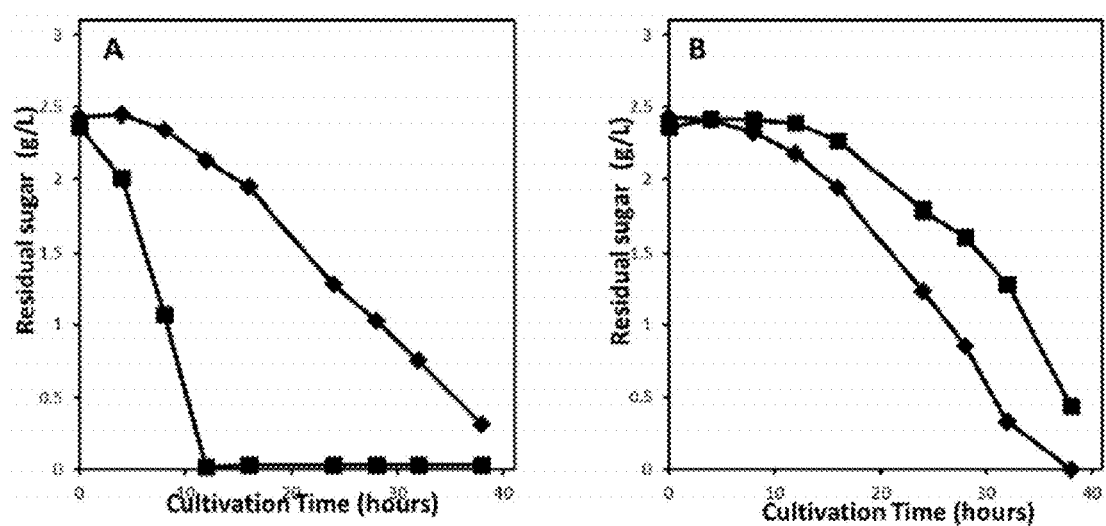
FIG. 6 shows the concentrations of the remaining cellobiose (♦) and xylose (■) in each medium after culturing CP12CHBASC (A) and CP12CHBASC/CRP* (B).

The results are shown in FIG. 6. The results of strains CP12CHBASC and CP12CHBASC/CRP* are found in FIGS. 6A and 6B, respectively where residual concentrations of cellobiose (diamond) and xylose (rectangle) are reported.

As shown in FIG. 6A, the CP12CHBASC strain was unable to utilize cellobiose in the presence of xylose, which indicates that carbon catabolite repression is still maintained in spite of constitutive expression of chb and asc operons. Meanwhile, when wild-type crp gene of CP12CHBASC was replaced with modified crp (crp*), as shown in FIG. 6B, the utilization rate of xylose was reduced, making cellobiose more preferred carbon source.

The results show that constitutive expression of chb and asc operons or mutation of crp gene was not sufficient enough to eliminate carbon catabolite repression completely.

Example 7

Preparation of Modified *E. Coli* Via Evolutionary Adaptation

The strain prepared in the Example 3 was serially subcultured every day in a cellobiose minimal medium while shaking at 200 rpm at 37° C. for 30 days. When the culture medium reached $OD_{600}$ of 1.0, the cells were transferred into a fresh medium and cultured. The strain prepared above was designated "CP12CHBASC30".

Example 8

Cellobiose and Xylose Utilization of Modified *E. Coli*

The utilization rate of xylose and cellobiose of "CP12CHBASC" strain obtained in Example 3 was compared with "CP12CHBASC" strain obtained in Example 7. In compliance with theoretical yields of intracellular metabolites, xylose was used at a concentration of 10 g/L whereas cellobiose was used at a concentration of 4 g/L. The residual concentrations of xylose and cellobiose were determined with varying incubation periods, as in Example 6.

Figure 7:
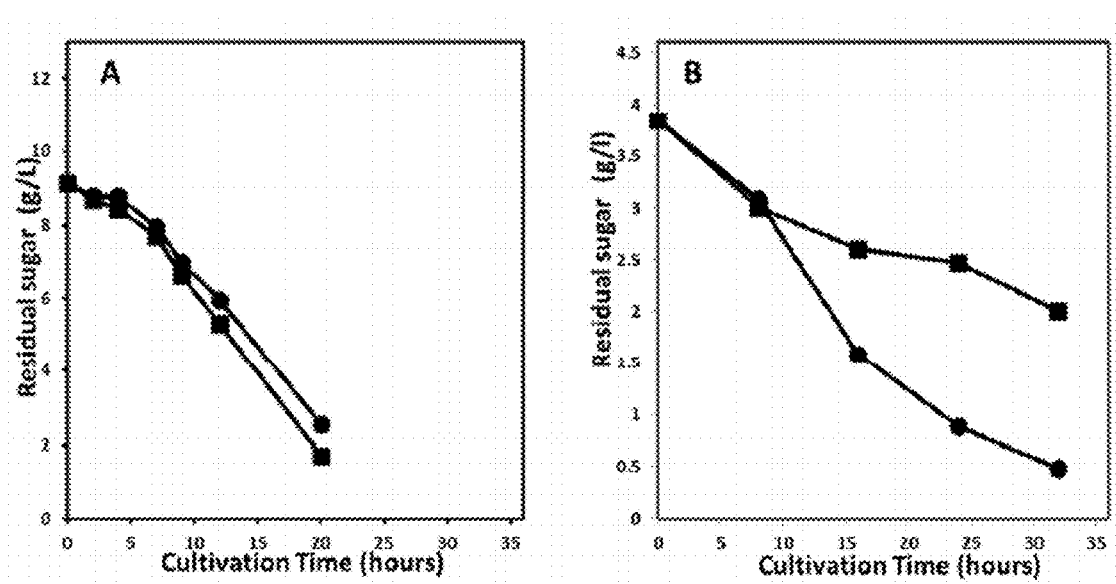
FIG. 7 shows xylose (A) and cellobiose (B) utilization rates of CP12CHBASC (■) and CP12CHBASC30 (●), where A indicates the concentration of remaining xylose after cultured in a medium containing xylose, and B indicates the concentration of remaining cellobiose after cultured in a medium containing cellobiose.

The results are shown in FIG. 7. The utilization rate of xylose and cellobiose are found in FIGS. 7A and 7B, respectively where strains of CP12CHBASC (rectangle) and CP12CHBASCK30 (circle) are reported.

As shown in FIG. 7, xylose utilization rate of both strains were similar. However, cellobiose utilization rate of CP12CHBASC30 was remarkably higher than that of CP12CHBASC. The results indicate that cellobiose utilization of *E. coli* can be enhanced through evolutionary adaptation as shown in Example 7.

Example 9

Cellobiose and Xylose Utilization of Modified *E. Coli*

In order to test simultaneous utilization of cellobiose and xylose in CP12CHBASC30 obtained in Example 7, the strain was cultured in media containing different concentrations of cellobiose and xylose and its utilization rate was measured. Three different media were used for the test: A) 2 g/L cellobiose and 2 g/L xylose; B) 3 g/L cellobiose and 2 g/L xylose; C) 1 g/L cellobiose and 1 g/L xylose. The residual concentrations of xylose and cellobiose were determined with varying incubation periods, as in Example 6.

Figure 8:
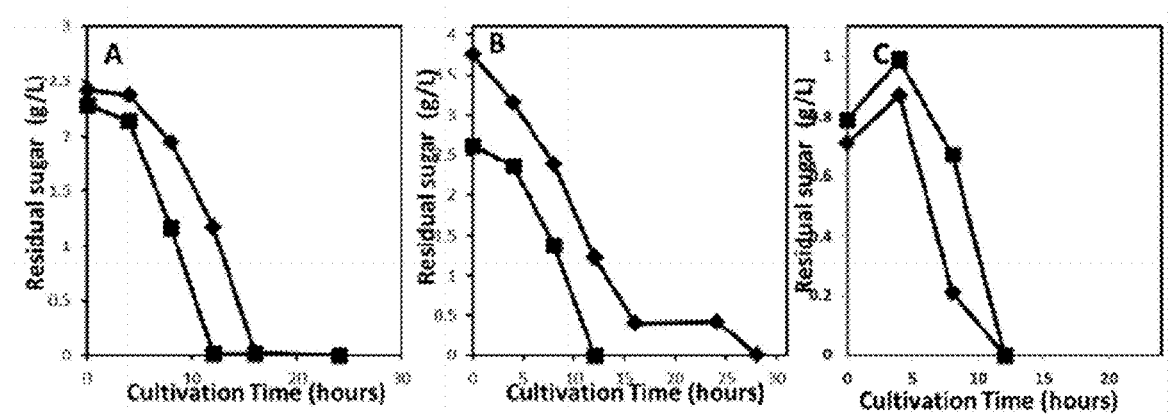
FIG. 8 shows the concentration of the remaining cellobiose (♦) and xylose (■) after culturing CP12CHBASC30 in various media (A: 2 g cellobiose+2 g xylose; B: 3 g cellobiose+2 g xylose; C: 1 g cellobiose+xylose).

The results are shown in the FIG. 8. The residual concentrations of xylose (rectangle) and cellobiose (diamond) in three different media were reported: FIG. 8A cellobiose 2 g/L, xylose 2 g/L; FIG. 8B cellobiose 3 g/L, xylose 2 g/L, FIG. 8C cellobiose 1 g/L, xylose 1 g/L.

As shown in FIG. 8, the CP12CHBASC30 of the present invention was shown to be capable of utilizing xylose and cellobiose simultaneously regardless of the concentrations of xylose and cellobiose Example 10

Gene Analysis of Modified *E. Coli* CP12CHBASC30

The modified strain CP12CHBASC30 of Example 7 was subjected to whole genome resequencing in Macrogen Inc. (Korea) and its gene sequence was compared with that of wild type *E. coli* MG1655.

It was found in the analysis that base 240 of gene yebK of the wild-type *E. coli* was changed from T to A via a point mutation (see SEQ ID NO: 9) which caused a codon change from TAT (codon for tyrosine) to TAA (end codon). This leads to a formation of a small protein consists of 79 amino acids (see SEQ ID NO: 10) instead of a YebK protein (SEQ ID NO: 8) with approximately 3,190 Da. The above result suggests that mutation of yebK gene can affect carbon metabolism in *E. coli*.

Example 11

Preparation of Modified *E. Coli* with Promoter Replacement and yebK Deletion (CP12CHBASCyebK-)

Based on the result of Example 10, a modified *E. coli* strain was obtained from the strain CP12CHBASC of Example 3, by deleting entire yebK gene (Accession Numbers: EG12860 (EcoCyc), b1853, ECK1854) in order to examine the effect of mutation in yebK gene on carbon metabolism. The new strain thus obtained was designated "CP12CHBASCyebK-".

Figure 9:
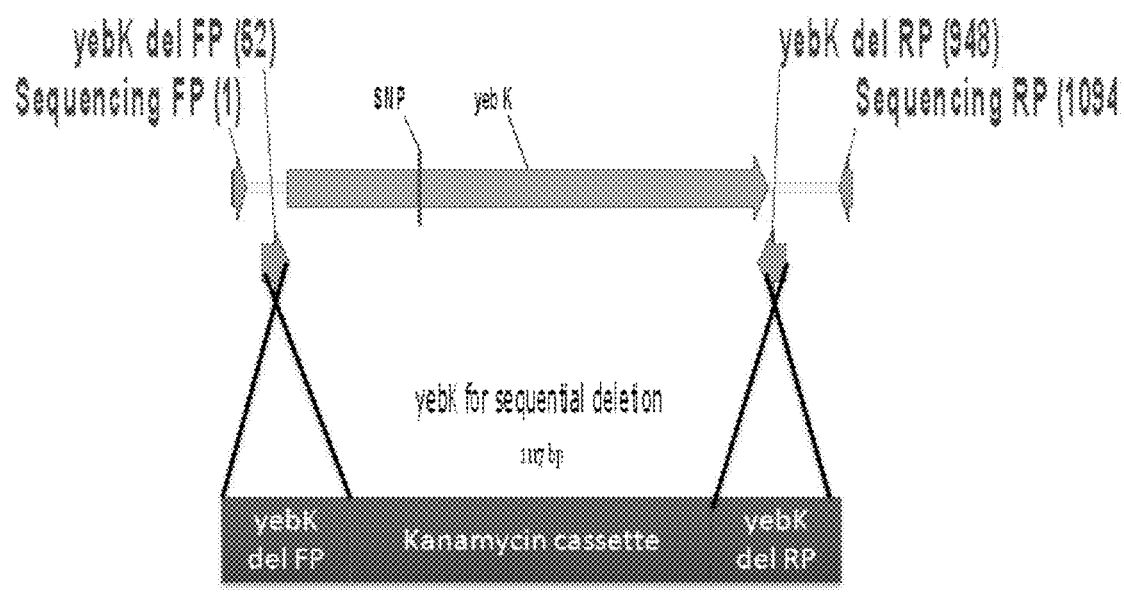
FIG. 9 shows a process of deleting yebK gene to produce CP12CHBASCyebK-strain in accordance with the present invention.

Specifically, yebK delFP (forward primer, SEQ ID NO: 11) complementary to a part starting from base 52 and yebK delRP (reverse primer, SEQ ID NO: 12) complementary to a part starting from base 948 were constructed, and PCR amplification, as described in FIG. 9, was carried out to replace yebK gene with kanamycin cassette. This gene substitution was confirmed by sequence analysis using forward primer (SEQ ID NO: 13) and reverse primer (SEQ ID NO: 14). The resulting *E. coli* with kanamycin cassette was then transformed with plasmid DNA pCP20, which expresses FLP recombinase, thereby removing kanamycin cassette via FLP recombination.

Example 12

Preparation of Modified *E. Coli* with Promoter Replacement, Adaptation in Cellobiose Minimal Medium and yebK Deletion (CP12CHBASCyebK-)

The process of Example 11 was repeated except for using CP12CHBASC30 strain instead of CP12CHBASC strain to obtain strain "CP12CHBASC30yebK-" whose yebK gene is deleted.

The modified *E. coli* strains obtained in Examples 3, 7, 11 and 12 and their descriptions are summarized in Table 2 below.

TABLE 2

| Example | Strain | Description |
| --- | --- | --- |
| — | *E. coli* MG1655 | Wild type |
| 3 | CP12CHBASC | Modified wild type MG1655 strain whose cryptic promoters of chb operon and asc operon were replaced with active CP12 promoters |
| 7 | CP12CHBASC30 | Modified CP12CHBASC strain adapted in a cellobiose minimal medium for 30 days |
| 11 | CP12CHBASCyebK- | Modified CP12CHBASC strain with yebK gene deletion |
| 12 | CP12CHBASC30yebK- | Modified CP12CHBASC30 strain with yebK gene deletion |

Example 13

Cellobiose and Xylose Utilization of Modified *E. Coli*

Utilization rates of cellobiose and xylose of modified *E. coli* strains CP12CHBASC, CP12CHBASC30, CP12CHBASCyebK-, and CP12CHBASC30yebK- obtained in Examples 3, 7, 11 and 12, respectively, were examined and compared. Based on the theoretical yield of cellular metabolites, concentration of 2 g/L xylose and 1 g/L cellobiose were used. Residual concentrations of xylose and cellobiose were measured based on incubation time.

Figure 10:
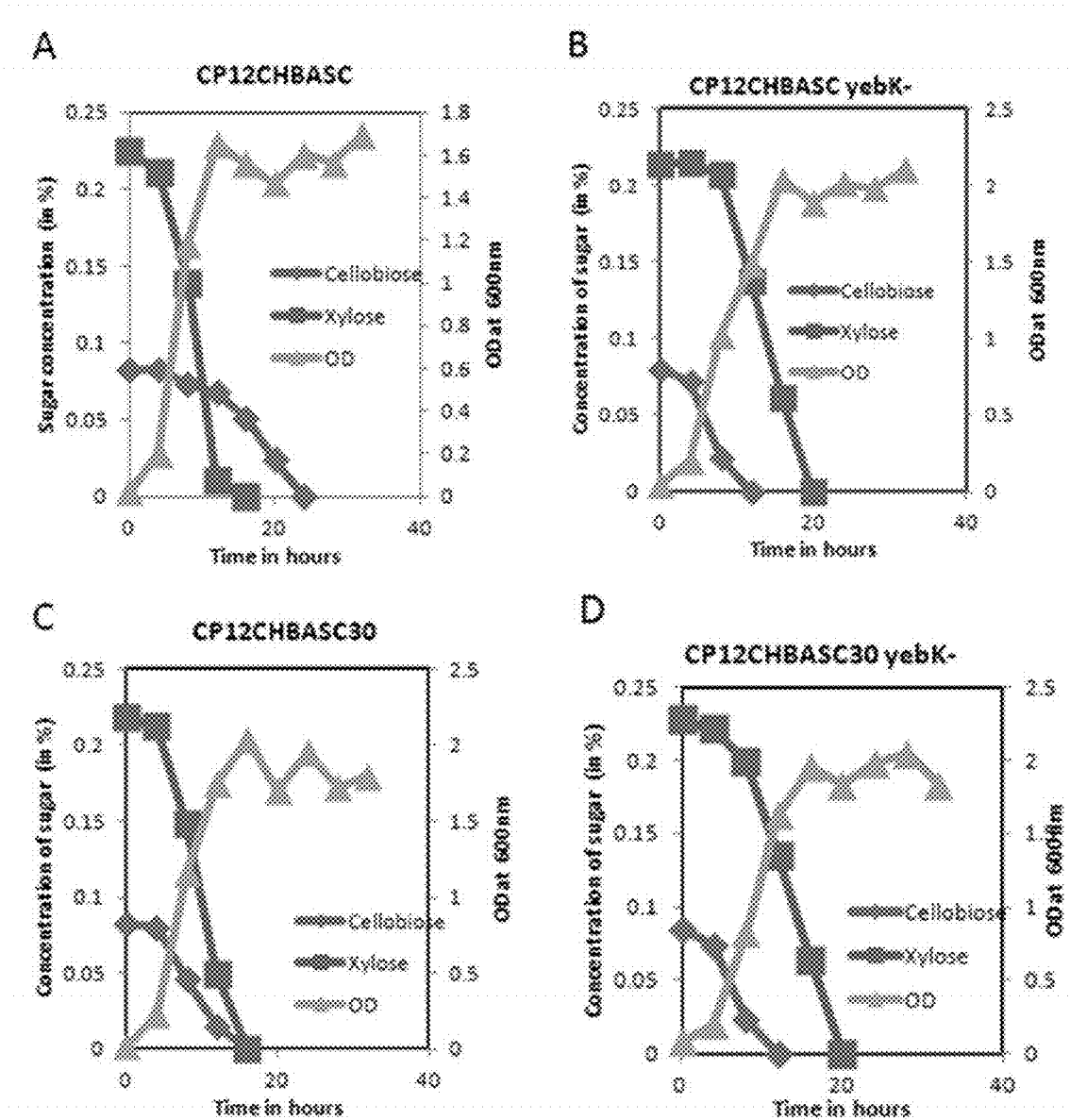
FIG. 10 illustrates simultaneous utilization rates of cellobiose and xylose by CP12CHBASC, CP12CHBASC30, CP12CHBASCyebK- and CP12CHBASC30yebK- as prepared in Examples 3, 7, 11 and 12, respectively.

The measurement results are shown in FIG. 10. FIGS. 10A, 10B, 10C, and 10D show the results of strain CP12CHBASC, CP12CHBASCyebK-, CP12CHBASC30, and CP12CHBASC30yebK-, respectively. In each figure, -♦- denotes concentration of cellobiose (ln %); -■-, xylose; and -▲-, optical density (OD).

As can be seen in FIG. 10, xylose and cellobiose utilization rates were higher in strains CP12CHBASC30, CP12CHBASCyebK- and CP12CHBASC30yebK- than in strain CP12CHBASC.

Example 14

Cellobiose and Other Sugars Utilization of Modified E. Coli

Utilization rates of cellobiose and other sugars of CP12CHBASC, CP12CHBASC30 and CP12CHBASCyebK- obtained in Examples 3, 7 and 11, respectively, were examined and compared. Experimental method was the same as in Example 13; and residual concentrations of cellobiose and other sugars were measured based on incubation time.

Figure 11:
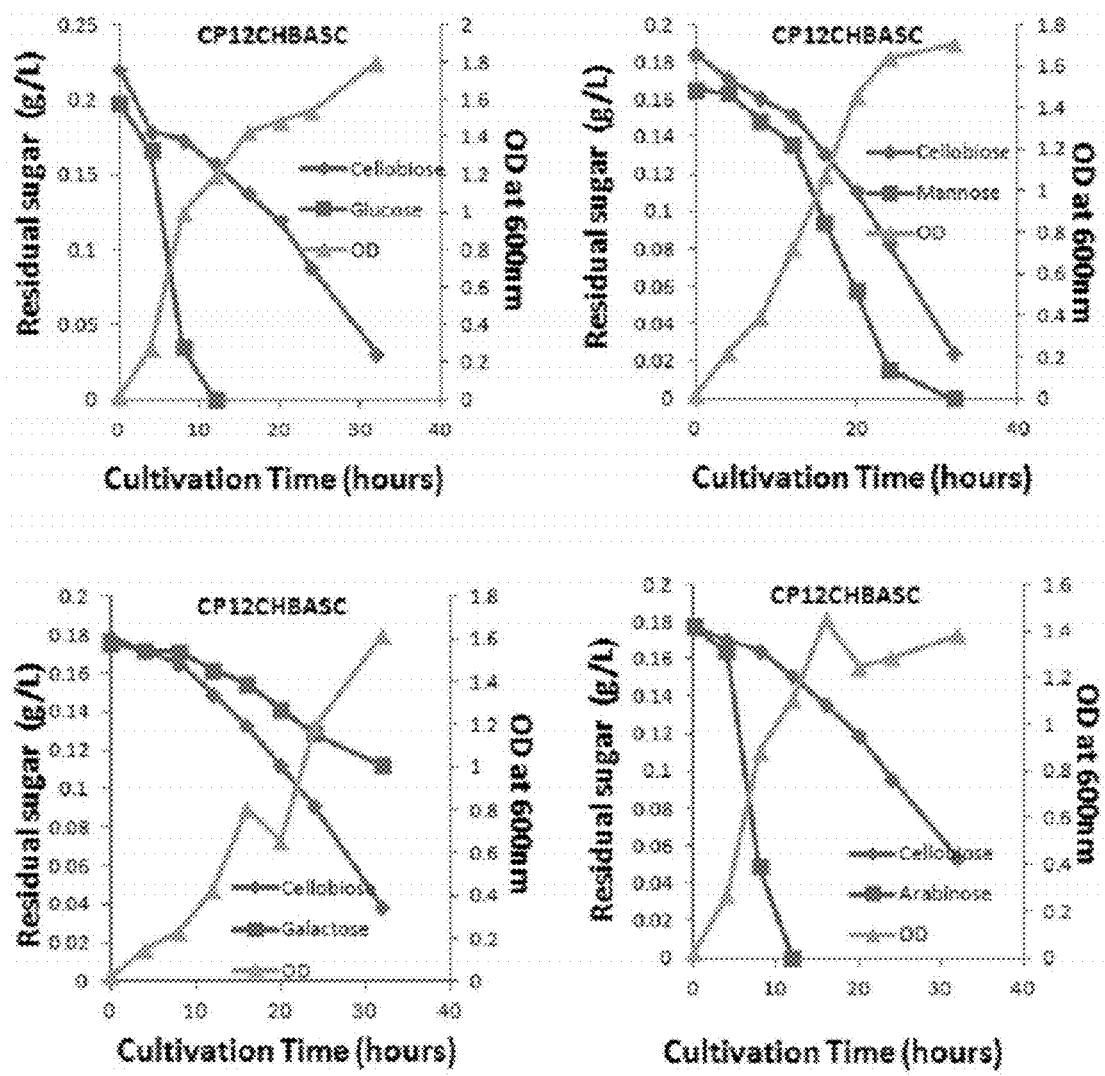
FIG. 11 illustrates simultaneous utilization rates of cellobiose and other sugars (glucose, mannose, galactose and arabinose) by CP12CHBASC obtained in Example 3.
Figure 12:
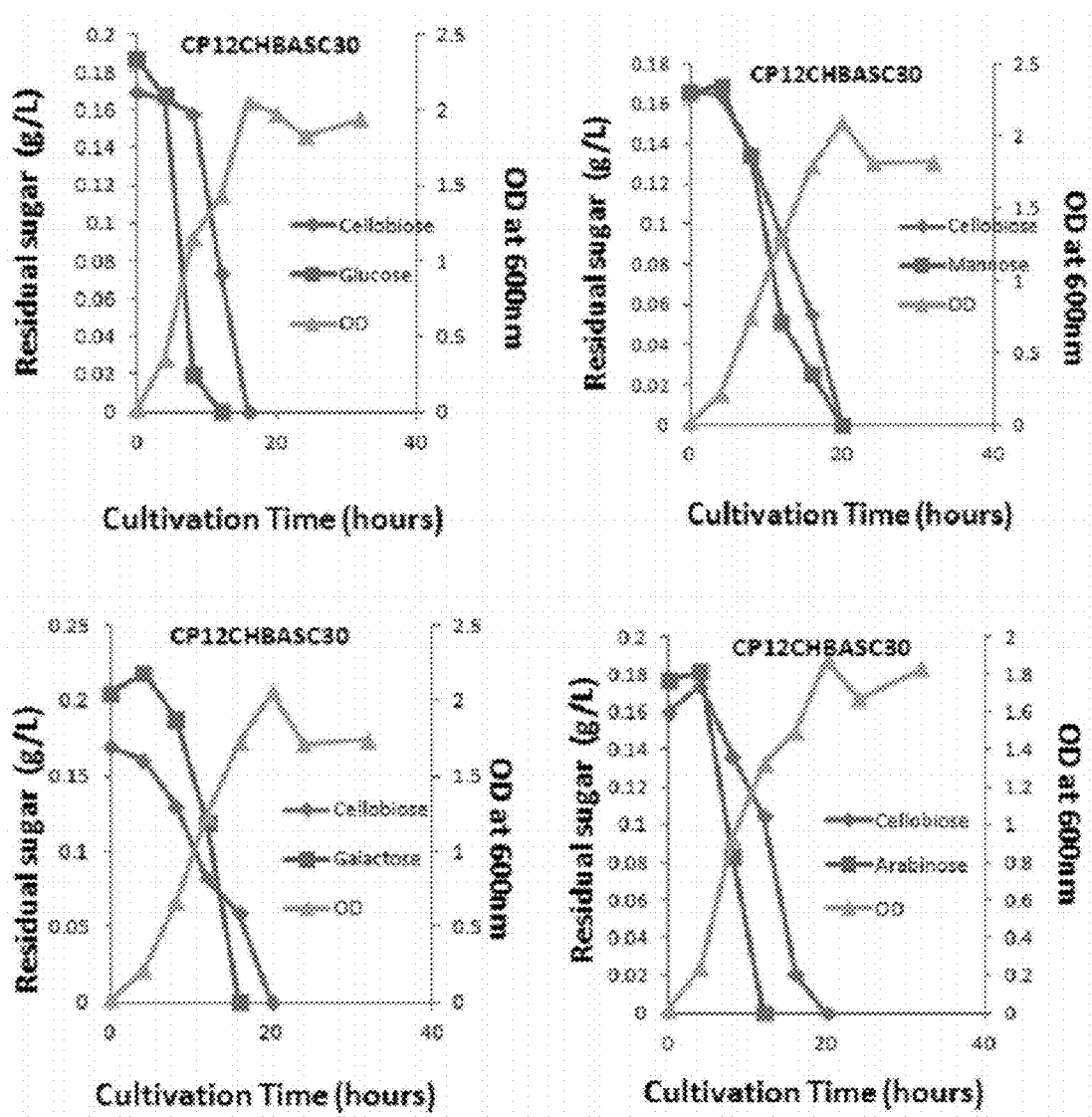
FIG. 12 illustrates simultaneous utilization rates of cellobiose and other sugars (glucose, mannose, galactose and arabinose) by CP12CHBASC30 obtained in Example 7.
Figure 13:
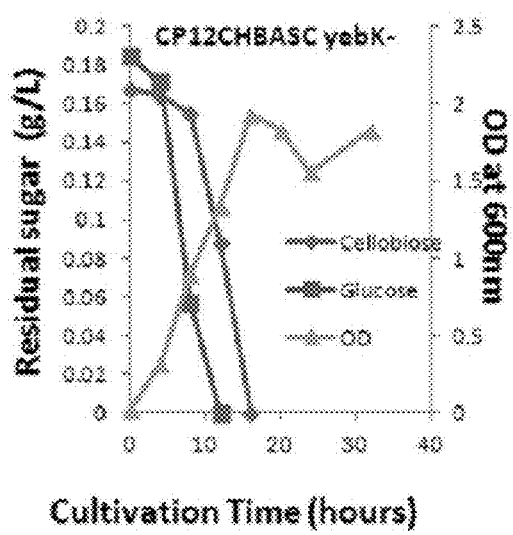
FIG. 13 illustrates simultaneous utilization rates of cellobiose and other sugars (glucose, mannose, galactose and arabinose) by CP12CHBASCyebK- obtained in Example 11.
Figure 13:
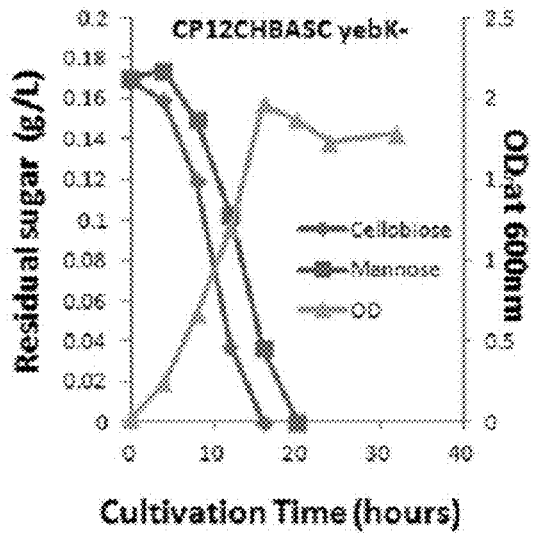
Figure 13:
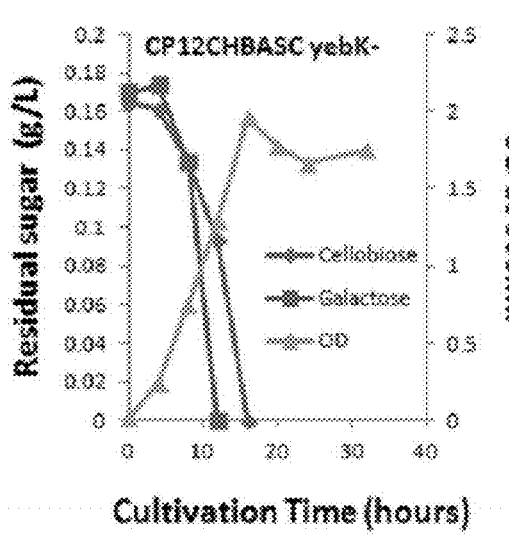
Figure 13:
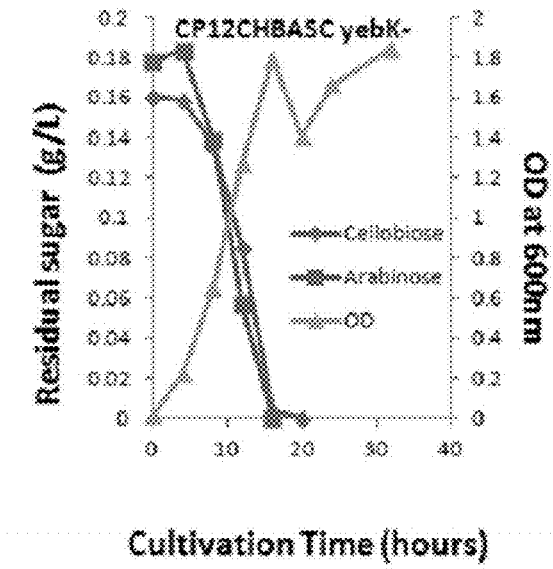

The results of simultaneous utilization rates of CP12CHBASC, CP12CHBASC30 and CP12CHBASCyebK- are shown in FIGS. 11, 12 and 13, respectively.

As can be seen in the above results, the simultaneous utilization rate of cellobiose and other sugars (glucose, mannose, galactose and arabinose) were remarkably enhanced in strains CP12CHBASC30 and CP12CHBASCyebK- than in strain CP12CHBASC. Test result proves that activation of cellobiose metabolism, pentose phosphate pathway and hexose phosphate pathway by a mutation of yebK gene allowed enhanced simultaneous utilization rate of cellobiose and other sugars.

Example 15

Growth Rate of Modified E. Coli Under Cellobiose and Xylose as Carbon Sources

In order to test growth rates under cellobiose and xylose as carbon sources, modified strains CP12CHBASC, CP12CHBASC30, CP12CHBASCyebK- and CP12CHBASC30yebK- obtained in Examples 3, 7, 11 and 12, respectively, were cultured separately on a medium containing either cellobiose or xylose. Culture process was conducted in the same way as in Example 13.

Figure 14A:
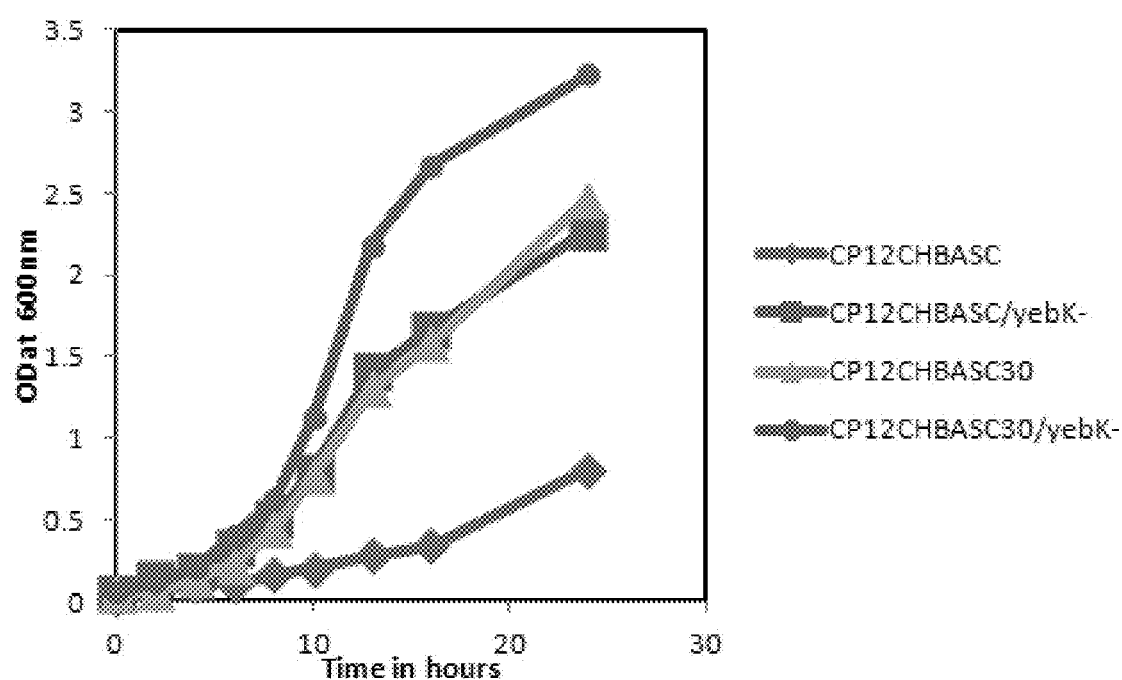
FIGS. 14A and 14B shows growth rates of CP12CHBASC, CP12CHBASC30, CP12CHBASCyebK- and CP12CHBASC30yebK- obtained in Examples 3, 7, 11 and 12, under cellobiose (14A) and xylose (14B) as a carbon source, respectively.
Figure 14B:
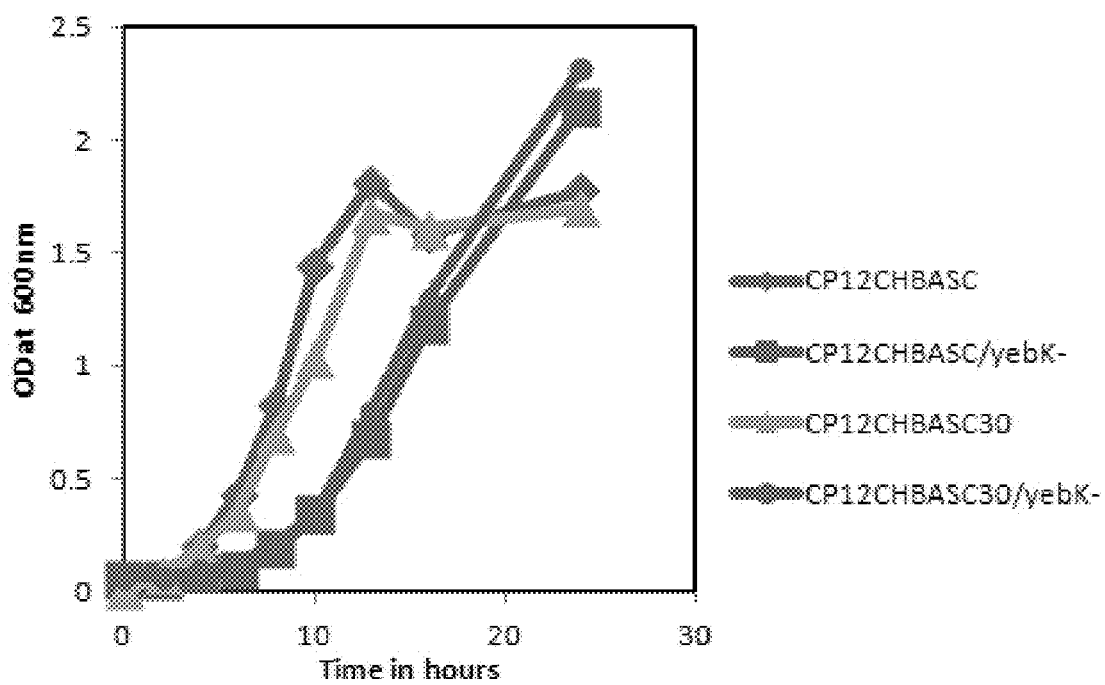

Growth curves on cellobiose and xylose were shown in FIG. 14A and FIG. 14B, respectively. As shown in FIG. 14A, when cellobiose was used as a carbon source, CP12CHBASCyebK- strains grew faster than CP12CHBASC strains and CP12CHBASC30yebK- strains grew faster than CP12CHBASC30 strains. Similarly, as shown in FIG. 14B, when xylose was used as a carbon source, strains CP12CHBASC and CP12CHBASC30 showed similar growth as wild-type, whereas growth of strains CP12CHBASCyebK- and CP12CHBASC30yebK- began after a long lag phase, indicating the direct role of yebK in regulating pentose utilization pathway or even the central carbon metabolism.

The results above demonstrate enhanced utilization rate of cellobiose as well as simultaneous utilization rate of cellobiose and xylose is achievable via deletion of yebK gene.

Example 16

Growth Rate of E. Coli Under Xylose as a Carbon Source

Figure 15:
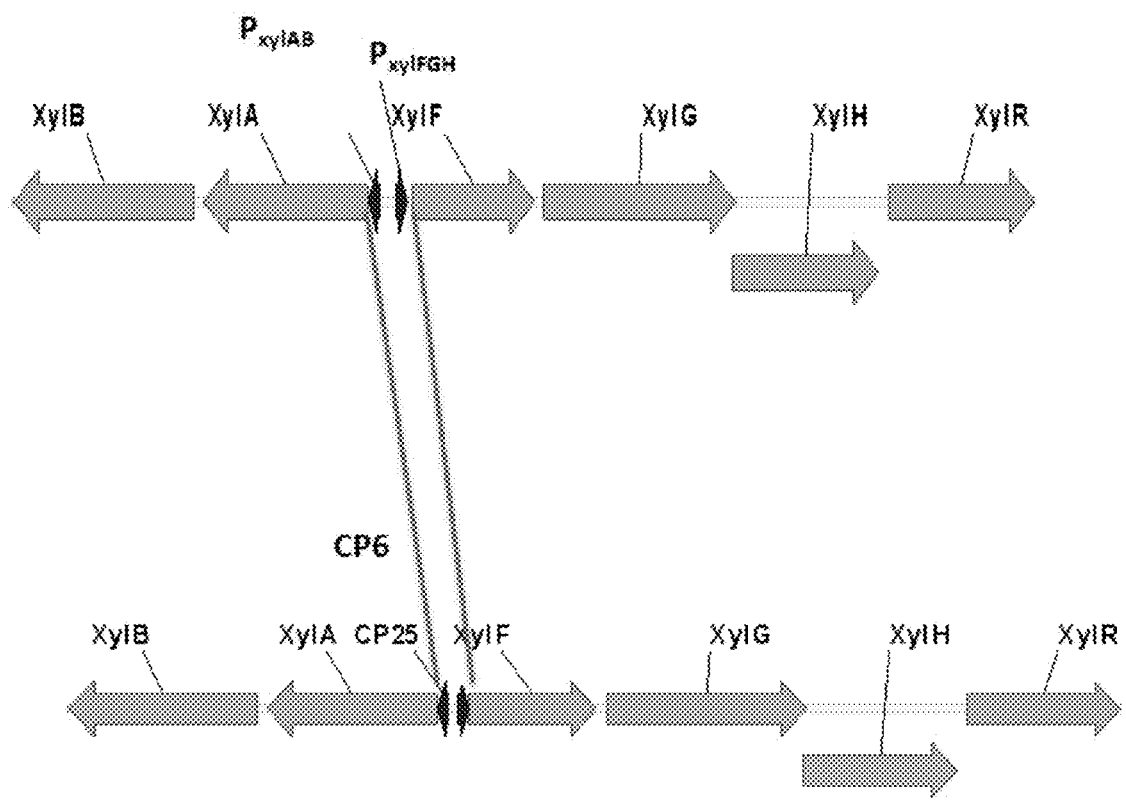
FIG. 15 illustrates a process of promoter replacement to produce CP25XylAB/CP6XylFGH of Example 16.

In order to examine the effect of yebK gene deletion on metabolism of xylose, a modified E. coli "CP12CHBASC/CP25XylAB/CP6XylFGH" was prepared by replacing inducible promoter XylAB/XylFGH (SEQ ID NO: 15) in E. coli with a constitutive promoter CP25XylAB/CP6XylFGH (SEQ ID NO: 16) which is related with xylose transport and metabolism. Promoter replacement process was conducted in the same way as Example 1, and the specific position of gene replacement is illustrated in FIG. 15. Forward primer (SEQ ID NO: 17) and reverse primer (SEQ ID NO: 18) were used for the above replacement. Meanwhile, the strain CP12CHBASCyebK- prepared in Example 11 was subjected to the same process of promoter replacement to prepare modified E. coli "CP12CHBASCyebK-/CP25XylAB/CP6XylFGH".

Figure 16:
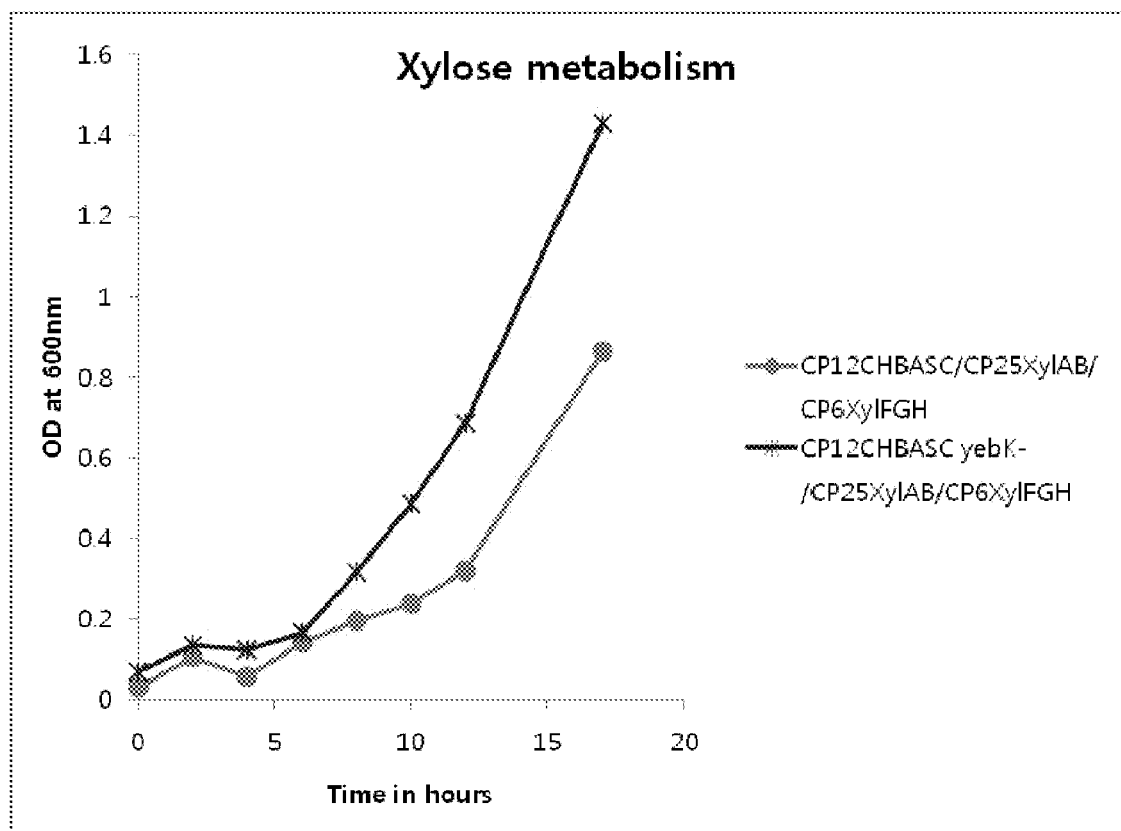
FIG. 16 shows growth rates of CP12CHBASCyebK-/CP25XylAB/CP6XylFGH and CP12CHBASC/CP25XylAB/CP6XylFGH obtained in Example 16 under xylose as a carbon source.

In order to test the growth rates of two above-mentioned strains under xylose as a carbon source, the strains were cultured on media containing 4 g/L of xylose. The results are shown in FIG. 16. As shown in FIG. 16, the growth rate of the strain whose yebK gene was deleted (CP12CHBASCyebK-/CP25XylAB/CP6XylFGH) was faster than the strain CP12CHBASC/CP25XylAB/CP6XylFGH. Thus, the increased growth rate caused by yebK gene deletion shows that yebK gene activates pentose phosphate pathway and involved in xylose transport and metabolism. Furthermore, it can be concluded that the deletion of yebK gene allowed an increase of cellobiose and xylose metabolism through the regulation of pentose phosphate pathway, which eventually lead to simultaneous utilization of cellobiose and xylose.

Example 17

Construction of Plasmid Expressing yebK

Figure 17:
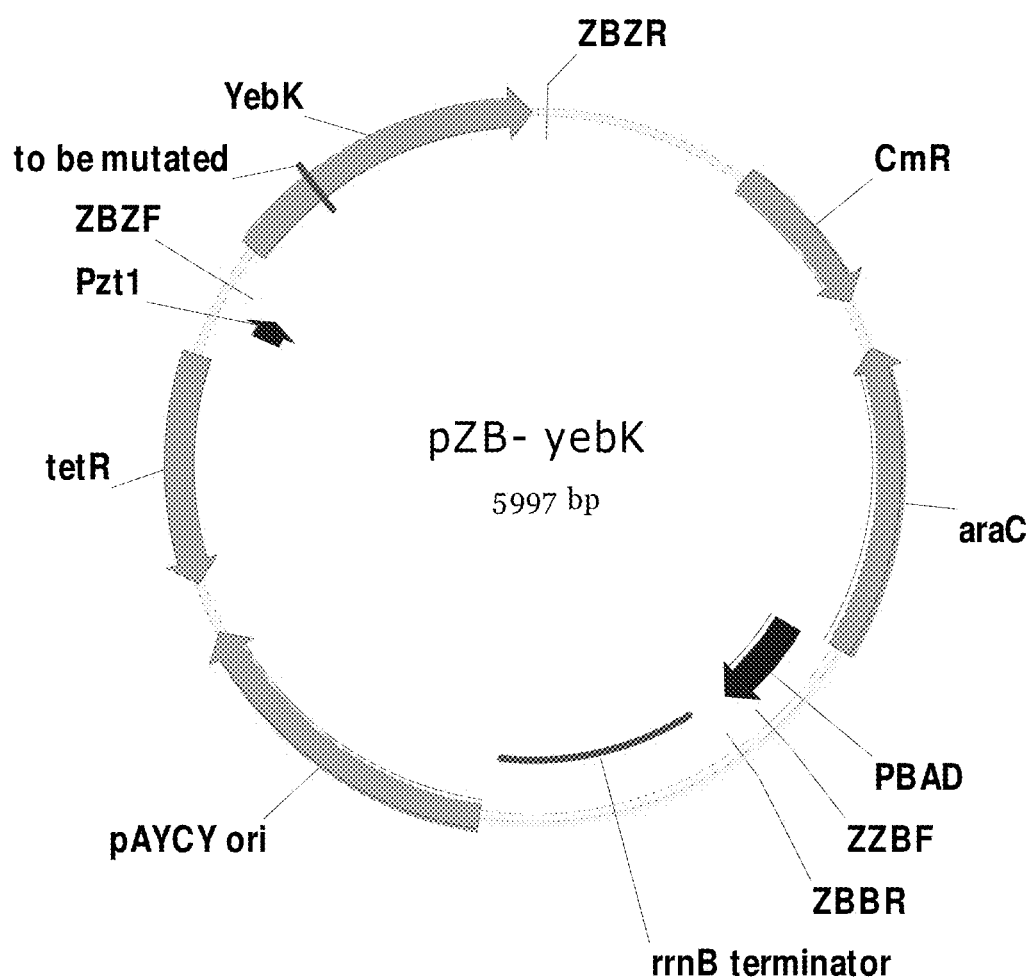
FIG. 17 illustrates the map of pZB-yebK, a plasmid expressing yebK. The yebK was cloned under the control of tetracycline promoter and in a low copy plasmid to avoid metabolic burden.

In order to perform a complementation test, a plasmid was constructed that expresses YebK from a tetracycline promoter. To do that, yebK gene was amplified from the genomic DNA of MG1655 with the primers set forth in SEQ ID NOs: 19 and 20. It was then cloned into the pZB plasmid using the restriction enzymes PstI and NheI. The plasmid thus obtained was designated "pZB-yebK," and represented in FIG. 17.

Example 18

Complementation of yebK

Figure 18:
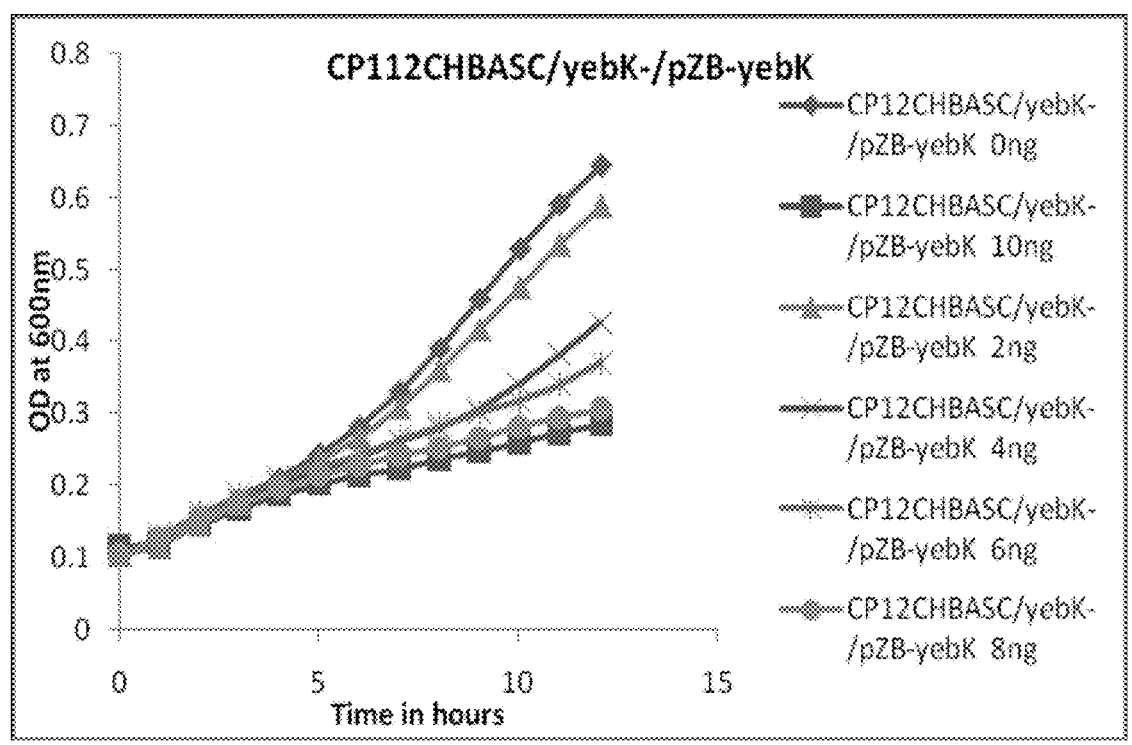
FIG. 18 shows growth rate of CP12CHBASC/yebK-/pZB-yebK obtained in Example 18 on a cellobiose minimal medium supplemented with varying concentrations of tetracycline (measured in TECAN microplate reader).

The plasmid "pZB-yebK" constructed in Example 17 was transformed into the mutant microorganism CP12CHBASC/yebK-. The cells (CP12CHBASC/yebK-/pZB-yebK) were grown on a cellobiose minimal medium supplemented with varying concentrations of tetracycline ranging from 0 ng/mL to 10 ng/mL. Growth on cellobiose was reduced with increasing concentration of tetracycline, indicating that yebK was directly regulating cellobiose metabolism (FIG. 18).

Example 19

Microarray Analysis of CP12CHBASC and CP12CHBASC30

Figure 19:
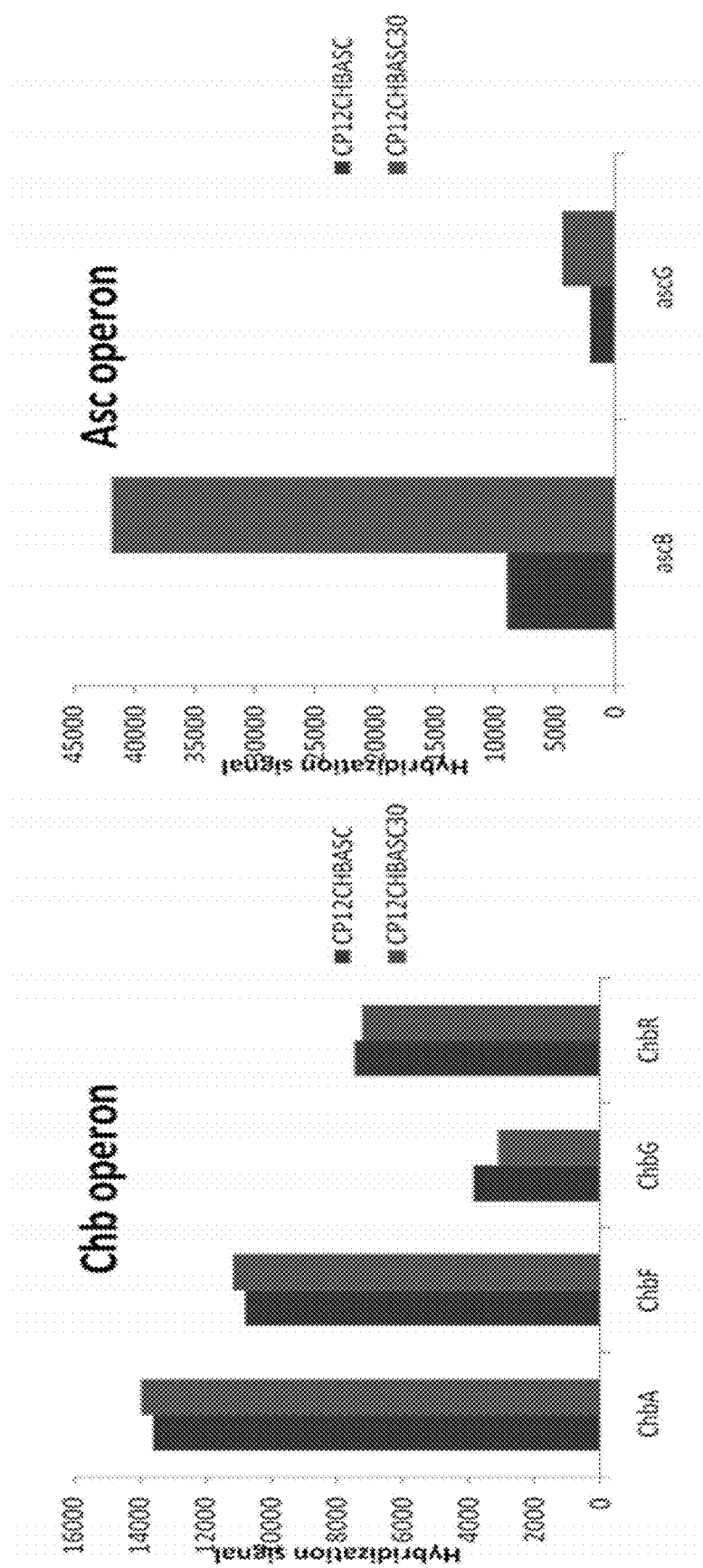
FIG. 19 shows the expression levels of all genes present in the chb and asc operons in CP12CHBASC and CP12CHBASC30 by microarray analysis.

Microarray analysis was performed to understand the global gene expression changes between the mutant microorganisms CP12CHBASC and CP12CHBASC30. The GE microarray, 3*20K (*E. coli* strain K12 MG1655) platform was used to analyze the mRNAs isolated from CP12CHBASC and CP12CHBASC30 grown on cellobiose minimal media. The results are shown in FIG. 19. Microarray data indicate that there was no huge difference in the expression of chb operon proteins between the two mutant strains. However, there was a huge difference in the expression level of AscB protein.

Example 20

RT-PCR for Determination of ascB Expression Level

RT-PCR for ascB was performed with the cDNA made from the total RNA isolated from the mutant organisms CP12CHBASC, CP12CHBASC/yebK-, CP12CHBASC30 and CP12CHBASC30/yebK- growing on cellobiose minimal media and using the primers in SEQ. ID NOs: 21 and 22. Total RNA was isolated from the mutant strains CP12CHBASC, CP12CHBASC30, CP12CHBASC/yebK- and CP12CHBASAC30/yebK-. Then, cDNA was synthesized from the total RNA using random hexamers and MuMLV reverse transcriptase. PCR was performed for the cDNA obtained as above and samples were withdrawn at 25, 27, 30 and 32 PCR cycles and run on 0.7% agarose gel.

Figure 20:
FIG. 20 illustrates the RT-PCR analysis to determine ascB expression level. Lane 1: Marker; Lanes 2 to 5: 25, 27, 30 and 32 cycles of ascB expression in CP12CHBASC; Lanes 6 to 9: 25, 27, 30 and 32 cycles of ascB expression in CP12CHBASC30; Lanes 10 to 13: 25, 27, 30 and 32 cycles of ascB expression in CP12CHBASC/yebK-; and Lanes 14 to 17: 25, 27, 30 and 32 cycles of ascB expression in CP12CHBASC30/yebK-.

Consistent with the microarray data, RT-PCR analysis indicates that the ascB expression level was higher in the mutant microorganisms CP12CHBASC/yebK-, CP12CHBASC30 and CP12CHBASC30/yebK- than in the mutant microorganism CP12CHBASC (FIG. 20). This might indicate that YebK is directly or indirectly regulating ascB expression. YebK might be directly controlling the promoter of ascB or might be controlling global RNAses and sRNAs, which in turn would be controlling ascB.

Example 21

Growth Rate of CP12ASC/yebK- on Cellobiose

Figure 21:
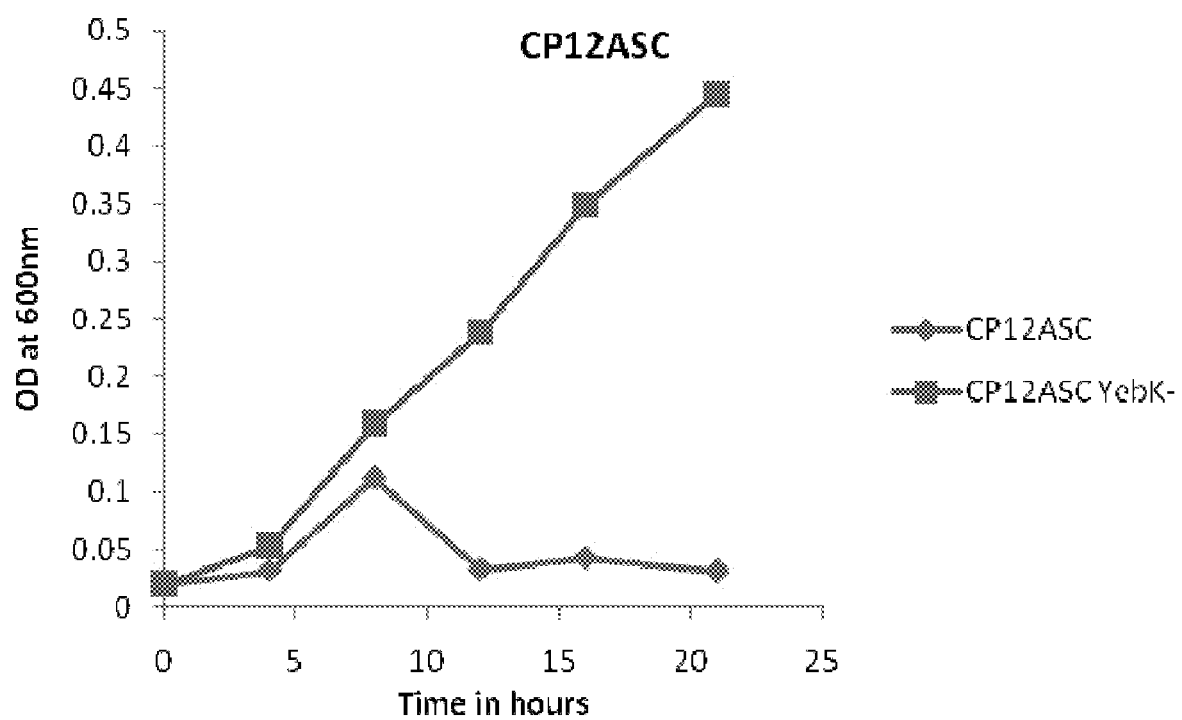
FIG. 21 shows growth rate of CP12ASC/yebK- on cellobiose.

Since ascB expression level was found to be higher in yebK deleted strains, it was assumed that deletion of yebK would help CP12ASC mutants to grow on cellobiose. Hence, yebK gene was deleted in the mutant microorganism CP12ASC in a manner similar to that described in example 11, and the resulting CP12ASC/yebK- and CP12ASC was compared for their growth rates (FIG. 21). The CP12ASC/yebK- was capable of growing on cellobiose minimal medium.

Example 22

Specific Activity of ascB

The expression level of ascB in CP12ASC was very low and hence the enzyme specificity could not be determined without strain as in example 4. However, ascB expression level was several folds higher in yebK- deleted strains and hence the strain CP12ASC/yebK- was used to determine the enzyme activity. β-Glucosidase assay was performed on the modified *E. coli* CP12ASC and CP12ASC/yebK- similar to that in Example 4. Exoglucanase assay was performed with p-Nitro phenyl cellobioside as a substrate. In brief, the strains were cultured in LB medium at 37° C. overnight, respectively. Then, 2 ml of the cell was lysed and suspended in 200 µL of 50 mM sodium phosphate buffer (pH 7.0). 100 µL of this crude cell extract was incubated with 400 µL of 10 mM p-Nitro phenyl cellobioside (PNPG) at 37° C. for 2 hours. 1 ml of 1M $Na_2CO_3$ was added thereto to stop the reaction and the absorbance was measured at 410 nm. One unit of the enzyme was defined as the amount of enzyme that liberated 1 µM of p-nitrophenol per minute. The absorbance was measured using a Biochrom Libra S22 spectrophotometer.

Figure 22:
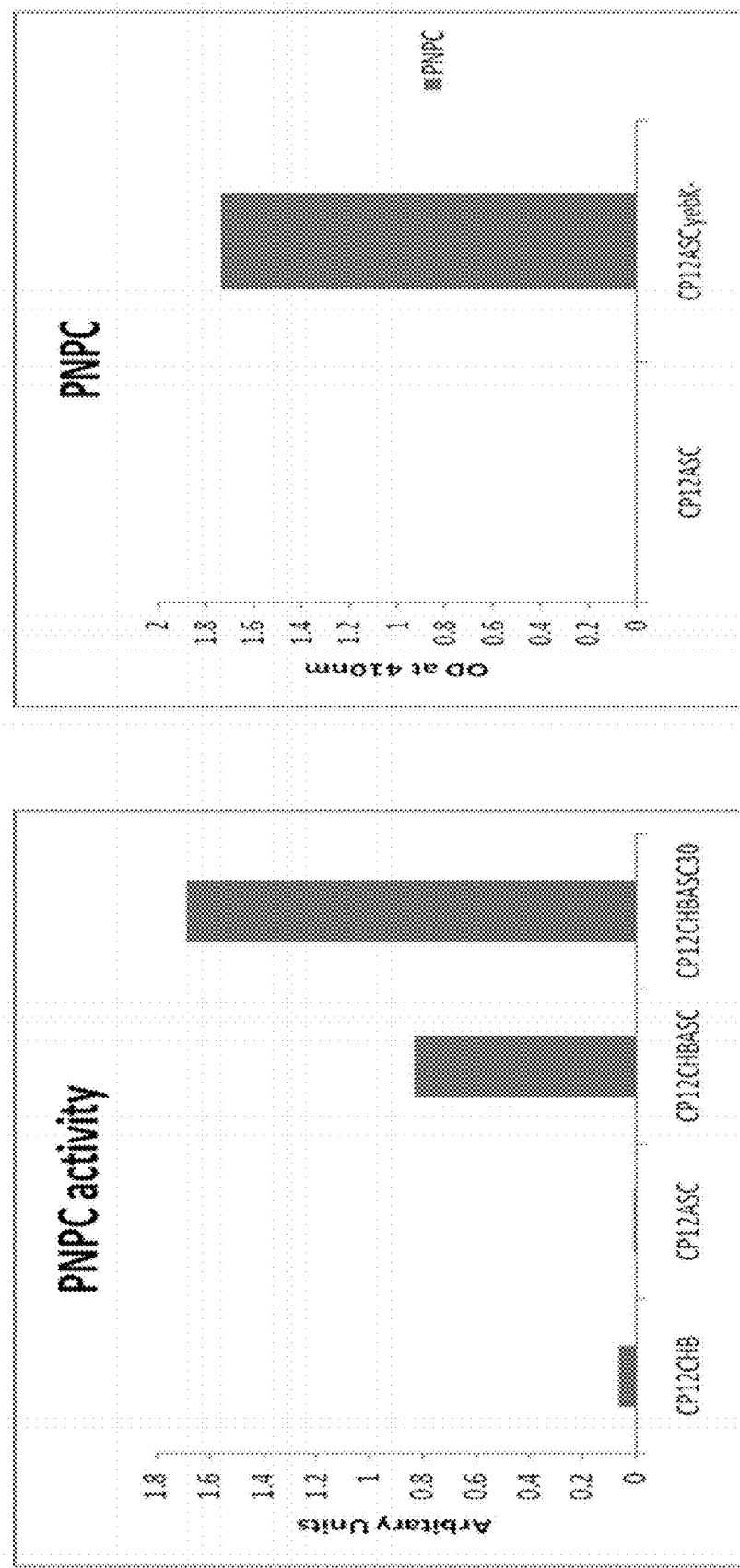
FIG. 22 shows specific activities of AscB using p-Nitro Phenyl β-cellobiose as a substrate.

Enzyme from CP12ASC/yebK- had activity against both PNPG and PNPC indicating that apart from the assigned β-glucosidase activity the strain might also have an exoglucanase activity capable of cleaving cellulo-oligosaccharides (FIG. 22).

---

What is claimed is:

1. A mutant microorganism comprising a chb operon and/or an asc operon, wherein said mutant microorganism possesses a mutation selected from:
   (a) replacement of the cryptic promoter of chb operon with an active promoter;
   (b) replacement of the cryptic promoter of asc operon with an active promoter; and (c) replacement of the cryptic promoters of chb operon and asc operon with active promoters.

2. The mutant microorganism of claim 1, further modified by:
   (d) a mutation of yebK gene, wherein an intact protein is not expressed from the mutated yebK gene.

3. The mutant microorganism of claim 1, wherein the wild-type microorganism is *E. coli*.

4. The mutant microorganism of claim 1, wherein the cryptic promoter of chb operon has the nucleotide sequence of SEQ ID NO: 1 and the cryptic promoter of asc operon has the nucleotide sequence of SEQ ID NO: 3.

5. The mutant microorganism of claim 1, wherein the active promoter is an inducible promoter or a constitutive promoter.

6. The mutant microorganism of claim 1, wherein the active promoter has the nucleotide sequence of SEQ ID NO: 2.

7. The mutant microorganism of claim 2, wherein the mutation of yebK gene is a point mutation or a deletion of entire yebK gene.

8. A method for preparing a mutant microorganism wherein said microorganism comprises a chb operon and/or an asc operon, said method comprising:
   (a) replacing one or more cryptic promoters of chb operon and asc operon with one or more active promoters.

9. The method of claim 8, which further comprises:
   (b) mutating yebK gene, wherein an intact protein is not expressed from the mutated yebK gene.

10. The method of claim 8, which further comprises:
    (c) culturing the mutant microorganism in a cellobiose minimal medium.

11. The method of claim 8, wherein the cryptic promoter of chb operon has the nucleotide sequence of SEQ ID NO: 1 and the cryptic promoter of asc operon has the nucleotide sequence of SEQ ID NO: 3.

12. The method of claim 8, wherein the active promoter is an inducible promoter or a constitutive promoter.

13. The method of claim 8, wherein the active promoter has the nucleotide sequence of SEQ ID NO: 2.

14. The method of claim 9, wherein the mutation of yebK gene is a point mutation or a deletion of entire yebK gene.

15. A method for producing biofuels, physiologically active materials, medicinal materials or industrial chemicals from biomass by employing a mutant microorganism of claim 1.

* * * * *